(12) United States Patent
Kahn et al.

(10) Patent No.: US 9,072,766 B2
(45) Date of Patent: Jul. 7, 2015

(54) METHODS OF TREATING OBESITY BY INHIBITING NICOTINAMIDE N-METHYL TRANSFERASE (NNMT)

(75) Inventors: Barbara B. Kahn, Cambridge, MA (US); Qin Yang, Brookline, MA (US); Daniel Kraus, Wurzberg (DE)

(73) Assignee: Beth Israel Deaconess Medical Center, Inc., Boston, MA (US)

( * ) Notice: Subject to any disclaimer, the term of this patent is extended or adjusted under 35 U.S.C. 154(b) by 0 days.

(21) Appl. No.: 13/885,284

(22) PCT Filed: Nov. 18, 2011

(86) PCT No.: PCT/US2011/061397
§ 371 (c)(1),
(2), (4) Date: May 14, 2013

(87) PCT Pub. No.: WO2012/068463
PCT Pub. Date: May 24, 2012

(65) Prior Publication Data
US 2013/0243790 A1 Sep. 19, 2013

Related U.S. Application Data

(60) Provisional application No. 61/415,111, filed on Nov. 18, 2010.

(51) Int. Cl.
| | | |
|---|---|---|
| *C12N 15/113* | (2010.01) | |
| *A61K 31/712* | (2006.01) | |
| *C12N 9/10* | (2006.01) | |
| *A61K 39/395* | (2006.01) | |

(52) U.S. Cl.
CPC .......... *A61K 31/712* (2013.01); *C12N 15/1137* (2013.01); *C12N 2310/11* (2013.01); *C12N 2310/14* (2013.01); *C12N 2310/16* (2013.01); *C12N 2310/315* (2013.01); *C12N 2310/321* (2013.01); *C12N 9/1007* (2013.01); *C12Y 201/01001* (2013.01); *A61K 39/3955* (2013.01)

(58) Field of Classification Search
None
See application file for complete search history.

(56) References Cited

U.S. PATENT DOCUMENTS

| | | | |
|---|---|---|---|
| 2003/0060438 A1* | 3/2003 | Henry et al. | 514/44 |
| 2005/0267023 A1* | 12/2005 | Sinclair et al. | 514/12 |

FOREIGN PATENT DOCUMENTS

WO 2009129544 10/2009

OTHER PUBLICATIONS

Aksoy, S., et al., "Human Liver Nicotinamide N-Methyltrasnferase: cDNA Cloning, Expression, and Biochemical Characterization," Journal of Biological Chemistry, American Society for Biochemistry and Molecular Biology, US, 269 (20) 14835-14840 (May 20, 1994).

Beales, P.E., et al., "Diet Can Influence the Ability of Nicotinamide to Prevent Diabetes in the Non-Obese Diabetic Mouse: A Preliminary Study," Diabetes/Metabolism Research and Reviews, 15(1): 21-28 (Jan. 1, 1999).

Jiang, G., et al., "Prevention of Obesity in Mice by Antisense Oligonucleotide Inhibitors of Stearoyl-CoA Desaturase-1," Journal of Clinical Investigation, American Society for Clinical Investigation, US, 115(4): 1030-1038 (Apr. 1, 2005).

Kraus, D., et al."Knockdown of Nicotinamide N-Methyltrasnferase (NNMT) Reverses Diet-Induced Obesity," Diabetes; 70th Annual Meeting of the American Diabetes-Association, American Diabetes Association, US; Orland, FL, USA, 59(1) p. A468 (Jun. 1, 2010).

Machen, J., et al., "Antisense Oligonucleosides Down-Regulating Costimulation Confer Diabetes-Preventative Properties to Nonobese Diabetic Mouse Dendritic Cells," The Journal of Immunology, the American Association of Immunologists, US, 173(1): 4331-4341 (Jan. 1, 2004).

Mou, B., et al., "Increased Expression and Possible Roles of Nicotinomide N-Methyltransferase in Pancreatic Islets of STZ-Induced Diabetic Monkeys," Chinese Journal of Pathophysiology, 23(5): 888-892 (Jan. 1, 2007).

Notification Concerning Transmittal of Copy of International Preliminary Report on Patentability, PCT/US2011/061397, "Methods of Treating Obesity by Inhibiting Nicotinamide N-Methyl Transferase (NNMT)," date of mailing May 30, 2013.

Notification of Transmittal of the International Search Report and the Written Opinion, PCT/US2011/061397, "Methods of Treating Obesity by Inhibiting Nicotinamide N-Methyl Transferase (NNMT)," date of mailing Jan. 14, 2013.

Sloop, K.W., et al., "Hepatic and Glucagon-Like Peptide-I-mediated Reversal of Diabetes by Glucagon Receptor Antisense Oligonucleotide Inhibitors," The Journal of Clinical Investigation, 113(11): 1571-1581 (Jun. 1, 2004).

Tang, S.W., et al., "Nicotinamide N-methyltrasnferase Induces Cellular Invasion Through Activating Matrix Metalloproteinase-2 Expression in Clear Cell Renal Carcinoma Cells," Carcinogenesis, 32:(2): 138-145 (Nov. 2, 2010).

Xu, J., et al., "Histone Deacetylase Inhibitor Depsipeptide Represses Nicotinamide N-Methyltransferase and Hepatocyte Nuclear Factor-1 Beta Gene Expression in Human Papillary Thyroid Cancer Cells," Thyroid, 16(2): 151-160 (Feb. 1, 2006).

\* cited by examiner

*Primary Examiner* — Tracy Vivlemore
(74) *Attorney, Agent, or Firm* — Hamilton, Brook, Smith & Reynolds, P.C.

(57) ABSTRACT

The present invention, in various embodiments, relates to methods of inhibiting NNMT production or activity in a cell, and methods of treating or preventing obesity or a related metabolic condition in a subject in need thereof, comprising administering a nicotinamide N-methyltransferase (NNMT) antagonist. The invention further provides methods of identifying NNMT antagonists useful for treating obesity and related metabolic disorders.

34 Claims, 20 Drawing Sheets

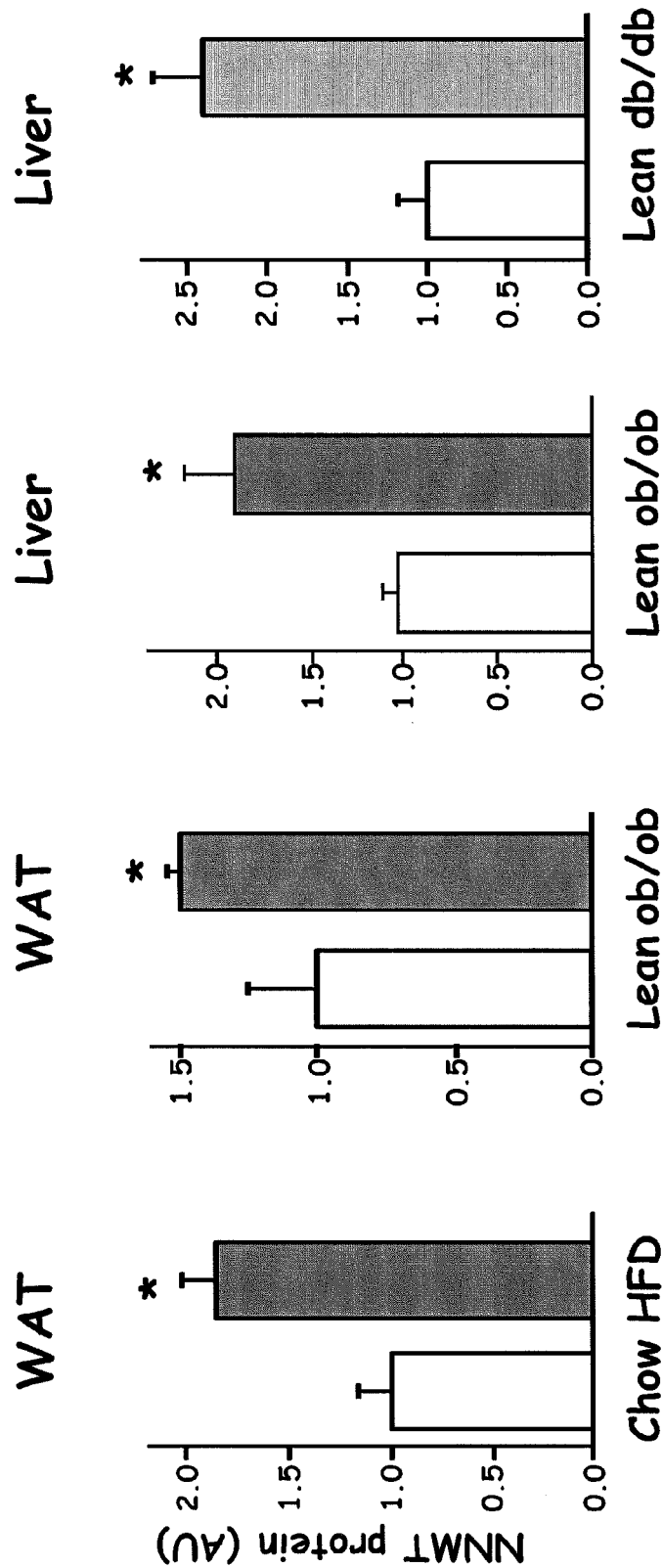

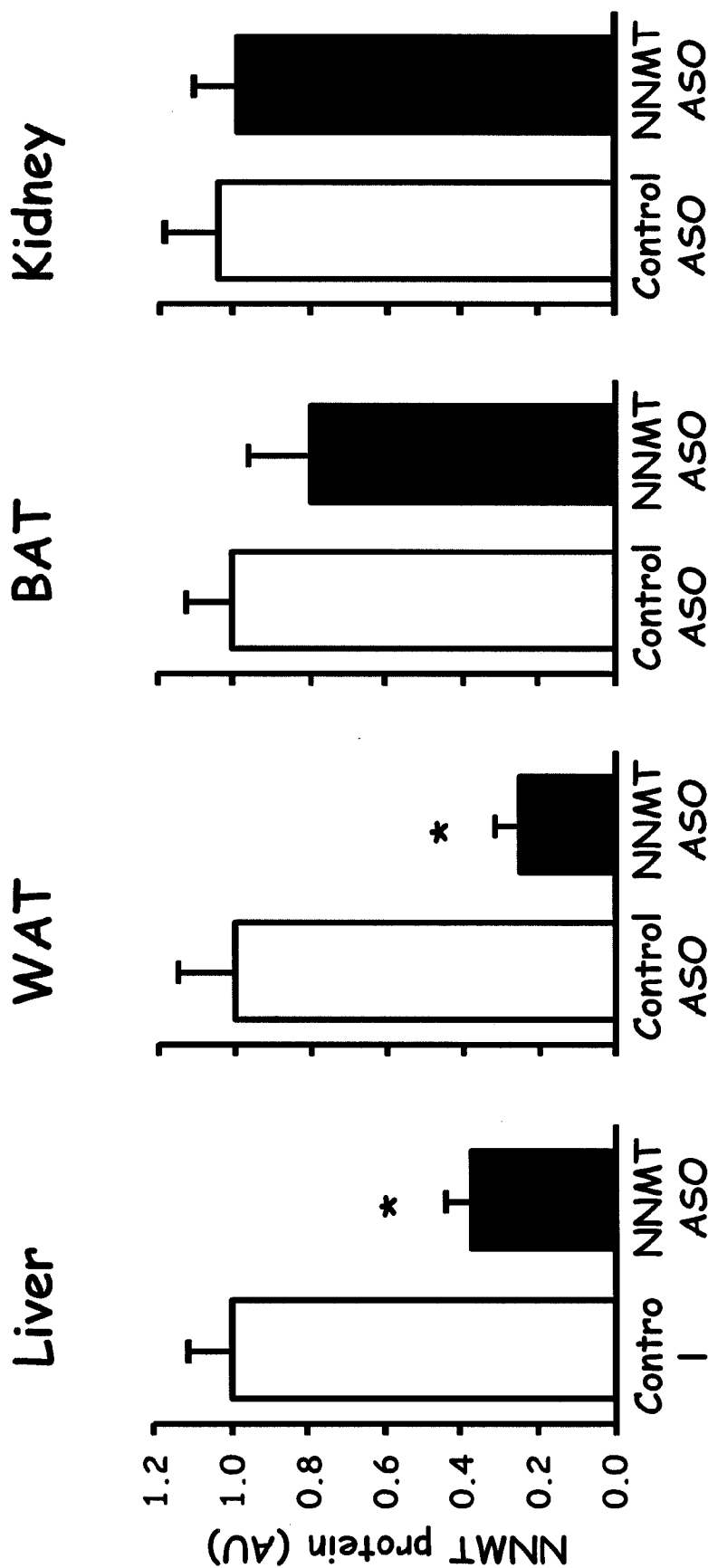

*p<0.05 versus Control ASO

*p<0.05 versus Control ASO

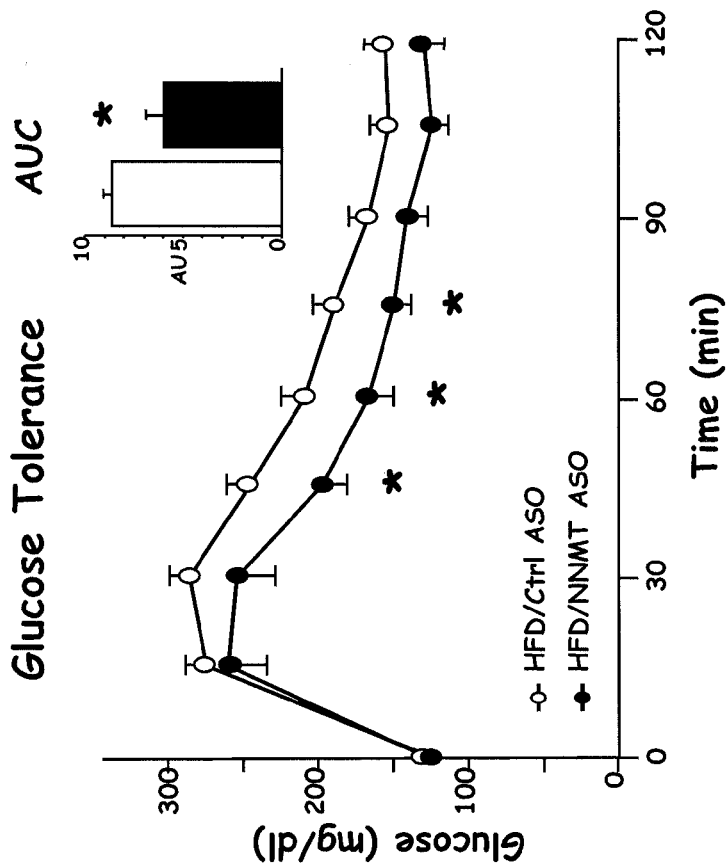
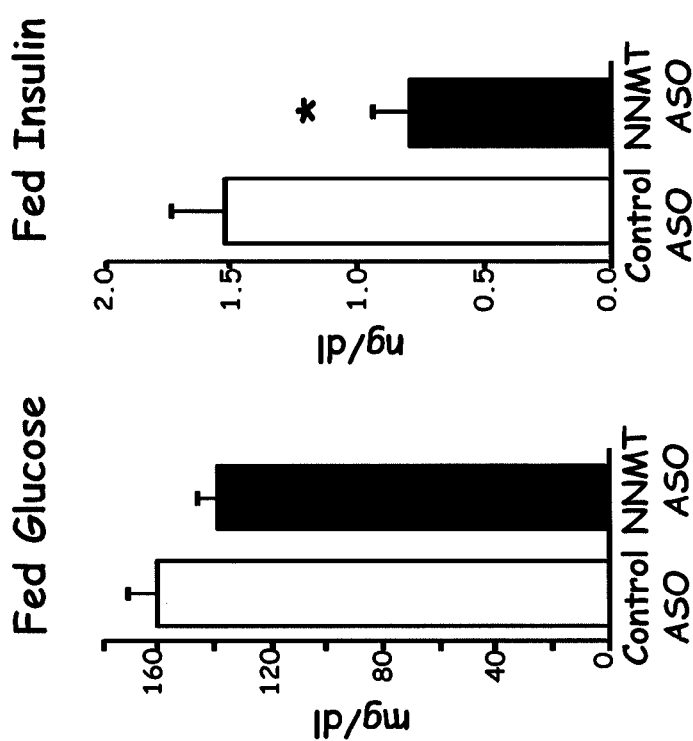
Figure 8A
Figure 8B
Figure 8C
*p<0.05 versus Control ASO

H & E stain of liver
White = lipid deposits

*p<0.05 versus Control ASO

No change in fecal lipids or body temperature. Implies increase in energy expenditure.

*p<0.05 versus Control ASO

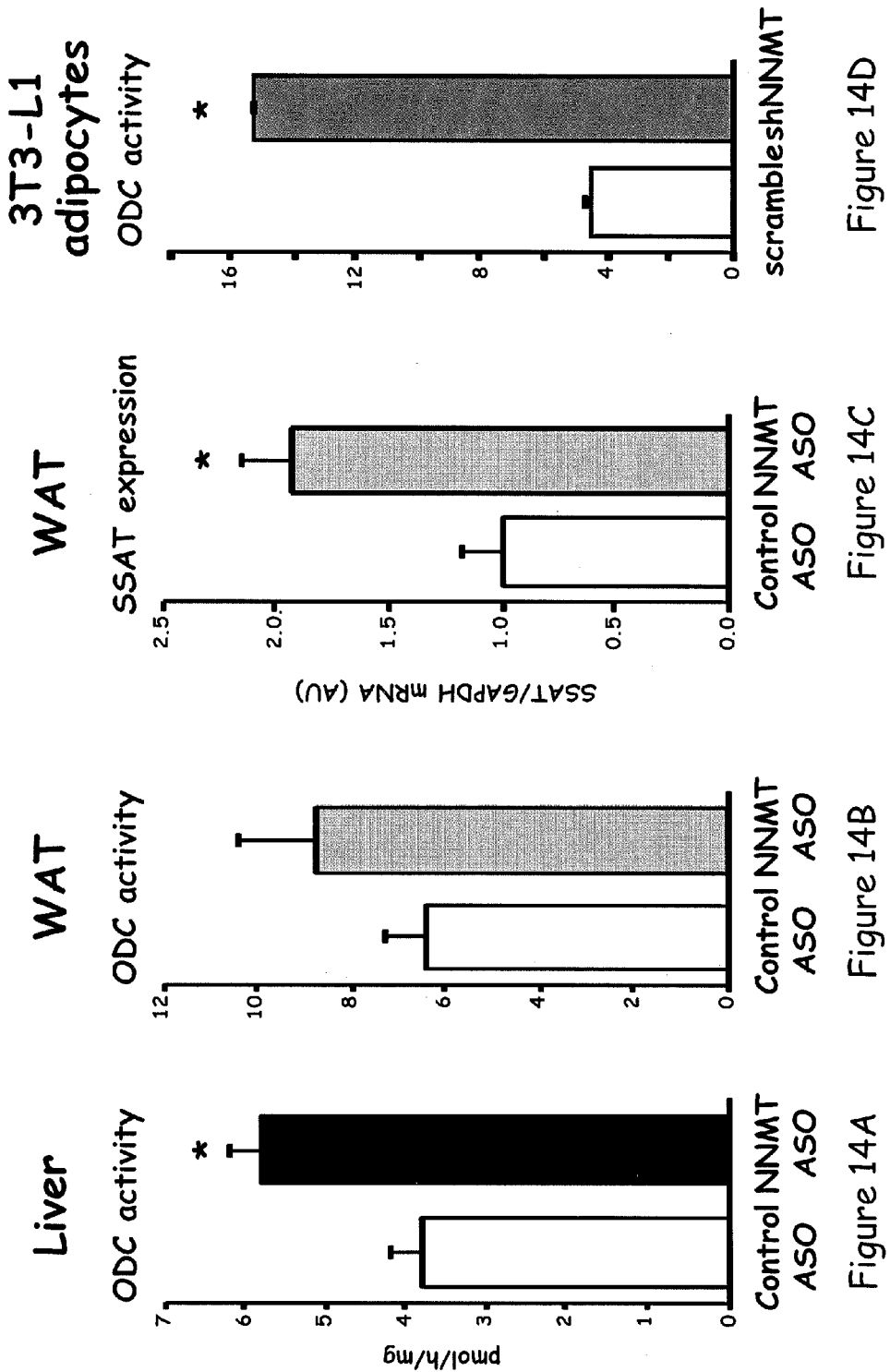

*p<0.05 versus no NMN
p<0.05 versus no DFMO

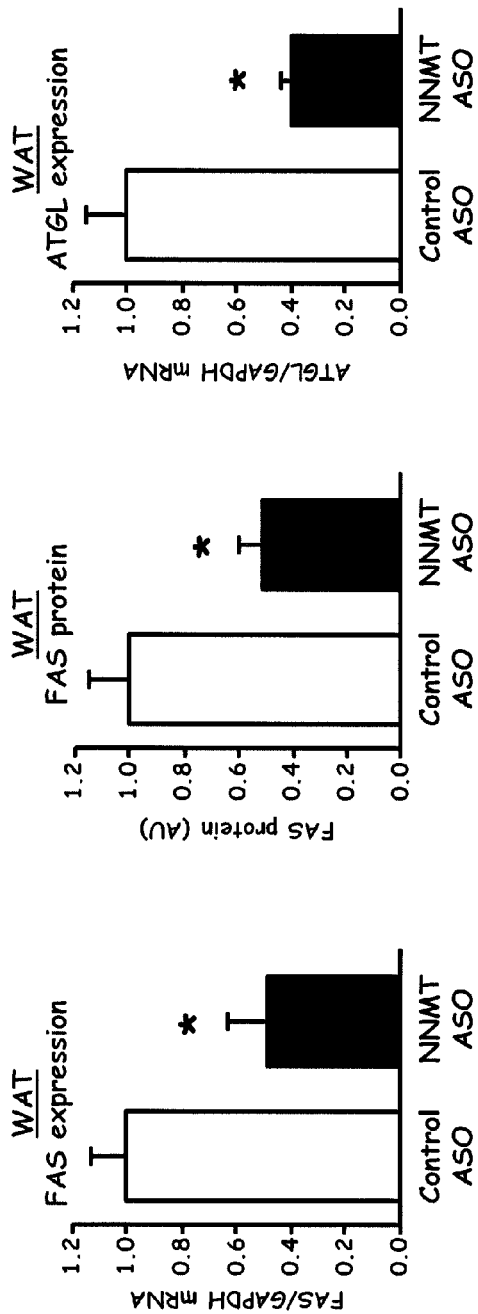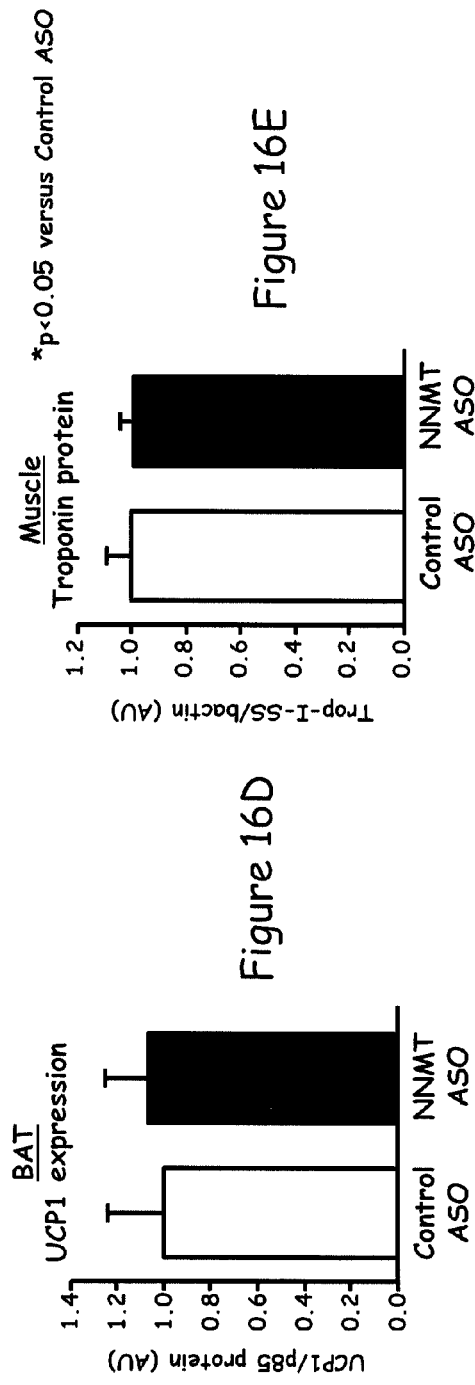

MESGFTSKDTYLSHFNPRDYLEKYYKFGSRHSAESQILKHLLKNLFKIF
CLDGVKGDLLIDIGSGPTIYQLLSACESFKEIVVTDYSDQNLQELEKWL
KKEPEAFDWSPVVTYVCDLEGNRVKGPEKEEKLRQAVKQVLKCDVTQ
SQPLGAVPLPPADCVLSTLCLDAACPDLPTYCRALRNLGSLLKPGGFL
VIMDALKSSYYMIGEQKFSSLPLGREAVEAAVKEAGYTIEWFEVISQSY
SSTMANNEGLFSLVARKLSRPL  (SEQ ID NO:1)

Figure 17

```
  1 gaggaggtgc ttgccagaca ctgggtcatg gcagtggtcg gtgaagctgc agttgcctag
 61 ggcagggatg gagagagagt ctgggcatga ggagagggtc tcgggatgtt tggctggact
121 agattttaca gaaagcctta tccaggcttt taaaattact ctttccagac ttcatctgag
181 actccttctt cagccaacat tccttagccc tgaatacatt tcctatcctc atctttccct
241 tctttttttt cctttctttt acatgtttaa atttaaacca ttcttcgtga cccctttct
301 tgggagattc atggcaagaa cgagaagaat gatggtgctt gttaggggat gtcctgtctc
361 tctgaacttt ggggtcctat gcattaaata atttttcctga cgagctcaag tgctccctct
421 ggtctacaat ccctggcggc tggccttcat cccttgggca agcattgcat acagctcatg
481 gccctccctc taccataccc tccaccccg ttcgcctaag ctcccttctc cgggaattc
541 atcatttcct agaacagcca gaacatttgt ggtctatttc tctgttagtg tttaaccaac
601 catctgttct aaaagaaggg ctgaactgat ggaaggaatg ctgttagcct gagactcagg
661 aagacaactt ctgcagggtc actccctggc ttctggagga aagagaagga gggcagtgct
721 ccagtggtac agaagtgaga cataatggaa tcaggcttca cctccaagga cacctatcta
```

Figure 18A

```
 781 agccatttta accctcggga ttacctagaa aaatattaca agttggttc taggcactct
 841 gcagaaagcc agattcttaa gcaccttctg aaaaatcttt tcaagatatt ctgcctagac
 901 ggtgtgaagg gagacctgct gattgacatc ggctctggcc ccactatcta tcagctcctc
 961 tctgcttgtg aatcctttaa ggagatcgtc gtcactgact actcagacca gaacctgcag
1021 gagctggaga agtggctgaa gaaagagcca gaggcctttg actggtcccc agtggtgacc
1081 tatgtgtgtg atctttgaagg aacagagtc aaggtccag agaaggagga gaagttgaga
1141 caggcggtca agcaggtgct gaagtgtgat gtgactcaga gccagccact gggggccgtc
1201 cccttacccc cggctgactg cgtgctcagc acactgtgtc tggatgccgc ctgcccagac
1261 ctccccacct actgcagggc gctcaggaac ctcggcagcc tactgaagcc aggggcttc
1321 ctggtgatca tggatgcgct caagagcagc tactacatga ttggtgagca gaagttctcc
1381 agcctccccc tgggccggga ggcagtagag gctgctgtga aagaggctgg ctacacaatc
1441 gaatggtttg aggtgatctc gcaaagttat tcttccacca tggccaacaa cgaaggactt
1501 ttctccctgg tggcgaggaa gctgagcaga cccctgtgat gcctgtgacc tcaattaaag
1561 caattccttt gacctgtca (SEQ ID NO:2)
```

METHODS OF TREATING OBESITY BY INHIBITING NICOTINAMIDE N-METHYL TRANSFERASE (NNMT)

RELATED APPLICATION

This application is the U.S. National Stage of International Application No. PCT/US2011/0641397, filed Nov. 18, 2011, which designates the U.S., published in English, and claims the benefit of U.S. Provisional Application No. 61/415,111, filed on Nov. 18, 2010. The entire teachings of the above applications are incorporated herein by reference.

GOVERNMENT SUPPORT

The invention was supported, in whole or in part, by NIDDK/NIH grant number DK43051 and a grant 09POST2250499 from American Heart Association. The Government has certain rights in the invention.

BACKGROUND OF THE INVENTION

Obesity is a chronic disease that contributes to numerous, often life-threatening medical conditions, including serious metabolic and cardiovascular diseases. The prevalence of obesity has steadily increased over recent years among various racial and ethnic groups, reaching epidemic proportions in the United States. Presently, more than 100 million adults in the United States are considered medically overweight or obese, making obesity a serious economic/healthcare burden and a leading cause of morbidity and mortality.

Obesity is considered to be a major risk factor for developing insulin resistance and type 2 diabetes. Increasing clinical evidence indicates that type 2 diabetes and other metabolic disorders related to obesity can be controlled through substantial and sustained weight loss. While diet and exercise are important in controlling weight and promoting weight loss in obese individuals, anti-obesity drugs can assist in mitigating the high morbidity and mortality caused by obesity and its associated conditions, particularly in individuals for which diet and exercise are not viable options. However, most approved anti-obesity drugs to date are not sufficiently effective in most individuals and/or produce undesirable or dangerous side effects.

In view of the increasing prevalence of obesity in the United States and other countries around the world, and the current lack of effective therapeutic agents for its treatment or prevention, there is a significant need for the identification of additional drug targets for the development of new, safe and effective anti-obesity drugs.

SUMMARY OF THE INVENTION

As shown herein, nicotinamide N-methyltransferase (NNMT) protein is increased in adipose tissue and liver in mouse models of insulin resistance. In addition, as described herein, decreasing NNMT expression using antisense oligonucleotides protects against diet-induced obesity, improves glucose homeostasis and reduces hepatic stress in mice on a high fat diet.

Accordingly, the present invention relates, in one embodiment, to a method of inhibiting the expression or activity of a nicotinamide N-methyltransferase (NNMT) protein in a cell, comprising providing the cell with an effective amount of at least one NNMT antagonist, wherein the NNMT antagonist inhibits production of NNMT protein, one or more activities of an NNMT protein, or a combination thereof. In particular embodiments, the cell is an adipocyte or a hepatocyte. In a specific embodiment, the NNMT antagonist is an antisense oligonucleotide.

In another embodiment, the invention relates to a method of treating or preventing obesity in a subject in need thereof, comprising administering to the subject an effective amount of a nicotinamide N-methyltransferase (NNMT) antagonist. In a particular embodiment, the NNMT antagonist is an antisense oligonucleotide.

In yet another embodiment, the invention relates to a method of treating or preventing a metabolic disorder in a subject in need thereof, comprising administering to the subject an effective amount of a nicotinamide N-methyltransferase (NNMT) antagonist, wherein the NNMT antagonist inhibits production of NNMT protein, one or more activities of an NNMT protein, or a combination thereof. The metabolic disorder can include one or more disorders selected from insulin resistance, type 2 diabetes, hyperglycemia and Metabolic Syndrome. In a particular embodiment, the NNMT antagonist is an antisense oligonucleotide.

In a further embodiment, the invention relates to a method of identifying a compound useful for treating obesity, comprising administering a test compound to a non-human animal, subsequently determining the expression or activity of NNMT in the animal following administration of the test compound and selecting a compound that inhibits the expression or activity of NNMT in the animal that has been administered the test compound. A decrease in the expression or activity of NNMT in the animal that has been administered the test compound relative to a control non-human animal that was not administered the test compound indicates the test compound is useful for treating obesity. In a particular embodiment, the test compound is an antisense oligonucleotide.

In an additional embodiment, the invention relates to a method of identifying a compound useful for treating obesity, comprising providing a sample of cells with a test compound, subsequently determining the expression or activity of N-methyltransferase (NNMT) in the sample in response to the test compound and selecting a test compound that inhibits the expression or activity of NNMT in the sample relative to a control sample of cells that was not provided with the test compound. A decrease in the expression or activity of NNMT in the sample that has been provided with the test compound relative to the control sample indicates the test compound is useful for treating obesity. In a particular embodiment, the test compound is an antisense oligonucleotide.

The present invention provides an important new therapeutic target for the identification of agents that can be used to treat obesity and in the development of treatments that alleviate or mitigate symptoms and diseases associated with obesity and related metabolic disorders such as insulin resistance, Metabolic Syndrome, and Type 2 diabetes.

BRIEF DESCRIPTION OF THE DRAWINGS

FIG. 3A is a graph depicting reduced NNMT mRNA expression in white adipose tissue of adipose-specific Glut4 overexpressing mice (AG4OX) with enhanced insulin sensitivity.

FIGS. 4A-D are graphs depicting increased levels of NNMT protein in white adipose tissue (WAT) (FIGS. 4A,B) and liver (FIGS. 4C,D) of mice in insulin resistant states (HFD, ob/ob, db/db) relative to non-insulin resistant states (Chow, Lean); HFD: High Fat Diet.

FIGS. 5A-D are graphs depicting levels of NNMT protein in different tissues of mice treated with NNMT antisense oligonucleotide (ASO) relative to controls. Treatment with NNMT ASO reduced levels of NNMT protein in liver (FIG. 5A) and white adipose tissue (WAT) (FIG. 5B) relative to controls, while treatment with NNMT ASO did not significantly reduce NNMT protein levels in brown adipose tissue (BAT) (FIG. 5C) or kidney tissue (FIG. 5D) of the treated mice relative to controls.

FIG. 6A: treatment of mice with NNMT ASO resulted in lower body weight relative to vehicle and control ASO treated mice. FIG. 6B: treatment of mice with NNMT ASO resulted in a lower fat mass percentage relative to control. FIG. 6C: treatment of mice with NNMT ASO resulted in a higher lean mass percentage relative to control.

FIGS. 8A-C are graphs showing that knockdown of NNMT expression using antisense oligonucleotide (ASO) improves glucose homeostasis in mice on a high fat diet. FIG. 8A shows glucose levels in ASO-treated mice fed glucose. FIG. 8B shows glucose levels in ASO-treated mice fed insulin and further shows that NNMT ASO treatment reduced glucose levels. FIG. 8C shows glucose levels over time in ASO-treated mice on a high fat diet and further shows that NNMT ASO treatment improved glucose tolerance.

FIG. 10A shows equivalent food intake in NNMT and Control ASO treated mice. FIG. 10B shows reduced feed efficiency in NNMT ASO-treated mice relative to control. FIG. 10C shows glucose reduced fat gain in NNMT ASO-treated mice relative to control.

FIG. 11A shows body weight change in NNMT and Control ASO treated mice fed high fat diets and untreated mice fed chow. FIG. 11B shows adiposity change in NNMT and Control ASO treated mice fed high fat diets and untreated mice fed chow. FIG. 11C shows lean mass change in NNMT and Control ASO treated mice fed high fat diets and untreated mice fed chow.

FIG. 12A: NNMT overexpression reduced oxygen consumption in hepatoma cells. FIG. 12B: NNMT knockdown using short hairpin (shNNMT) oligonucleotide increased oxygen consumption in hepatoma cells. FIG. 12C: Inhibition of NNMT activity using NMN, an inhibitor of NNMT, increased oxygen consumption in adipocytes.

FIGS. 14A-D are graphs showing that NNMT knockdown using NNMT ASO activates polyamine metabolism. FIG. 14A: NNMT knockdown using NNMT ASO activates polyamine metabolism in liver as measured by ODC activity. FIG. 14B: NNMT knockdown using NNMT ASO did not significantly affect polyamine metabolism in white adipose tissue (WAT) as measured by ODC activity. FIG. 14C: NNMT knockdown activates polyamine metabolism in WAT as measured by SSAT expression. FIG. 14D: NNMT knockdown using shNNMT activates polyamine metabolism in 3T3-L1 adipocytes as measured by ODC activity.

FIG. 15A: DFMO treatment blocks the NMN-mediated increase in $O_2$ consumption (compare yellow bar to green bar). FIG. 15B: DFMO treatment blocks the NMN-mediated increase in glucose uptake under basal (no insulin) conditions (compare yellow bar to green bar). FIG. 15C: DFMO treatment blocks the NMN-mediated increase in glucose uptake under Submax insulin stimulation conditions (compare yellow bar to green bar), while co-administration of NMN and DFMO increase glucose uptake relative to treatment with DFMO alone.

FIG. 16A is a graph depicting reduced fatty acid synthase (FAS) mRNA expression in white adipose tissue (WAT) of mice treated with NNMT ASO relative to control. NNMT knockdown reduced FAS expression in WAT.

FIG. 16B is a graph depicting reduced fatty acid synthase (FAS) protein levels in white adipose tissue (WAT) of mice treated with NNMT ASO relative to control. NNMT knockdown reduced FAS protein levels in WAT.

FIG. 16C is a graph depicting reduced ATGL mRNA expression in white adipose tissue (WAT) of mice treated with NNMT ASO relative to control. NNMT knockdown reduced ATGL expression in WAT.

FIG. 16D is a graph depicting equivalent ATGL protein levels in brown adipose tissue (BAT) of mice treated with NNMT ASO or Control ASO.

FIG. 16E is a graph depicting equivalent troponin protein levels in brown muscle tissue of mice treated with NNMT ASO or Control ASO.

FIG. 17 depicts the amino acid sequence of human NNMT (SEQ ID NO:1).

FIGS. 18A and B depict the cDNA nucleotide sequence corresponding to human NNMT mRNA (SEQ ID NO:2).

DETAILED DESCRIPTION OF THE INVENTION

Figure 1:
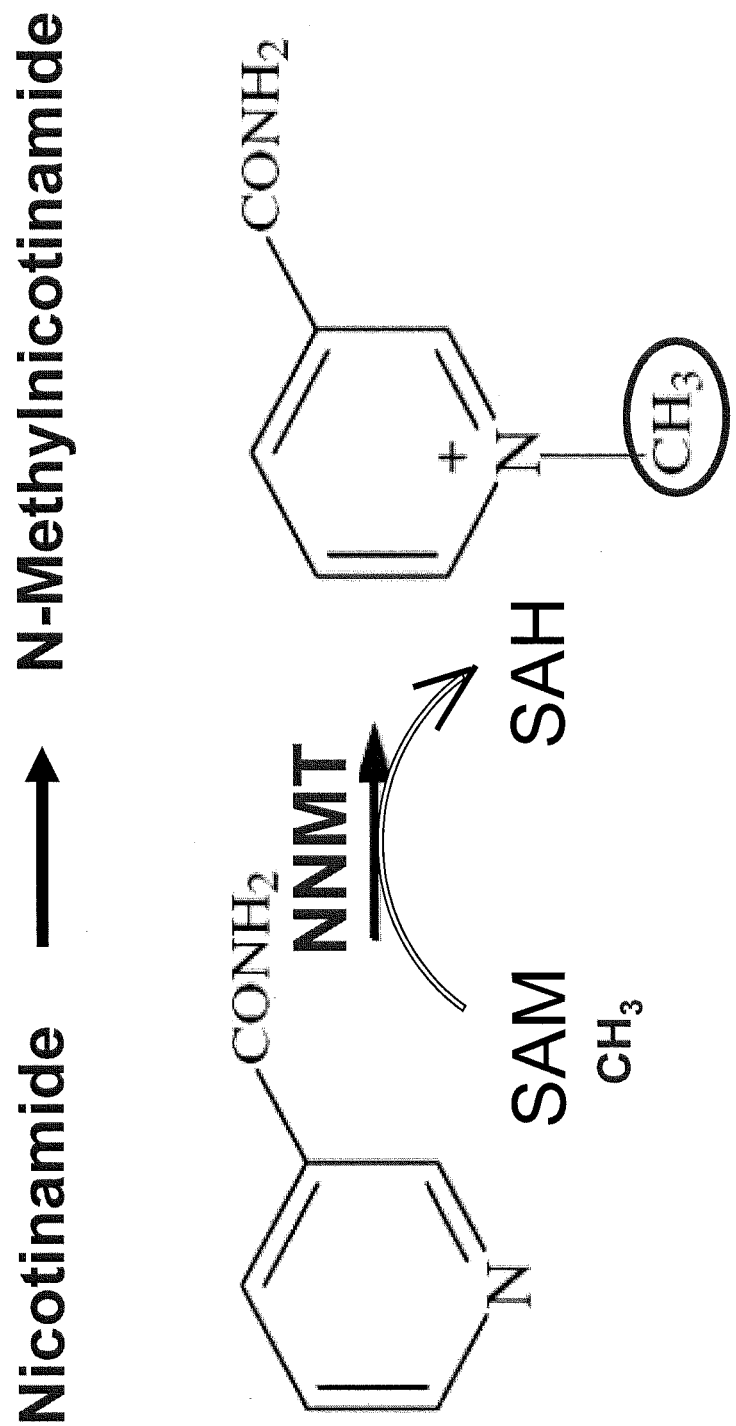
FIG. 1 is a schematic depicting NNMT-mediated catalysis of the methylation of nicotinamide to produce N-methylnicotinamide.

Unless defined otherwise, all technical and scientific terms used herein have the same meaning as commonly understood by one of ordinary skill in the art (e.g., in cell culture, molecular genetics, nucleic acid chemistry, hybridization techniques and biochemistry). Standard techniques are used for molecular, genetic and biochemical methods (see generally, Sambrook et al., Molecular Cloning: A Laboratory Manual, 2d ed. (1989) Cold Spring Harbor Laboratory Press, Cold Spring Harbor, N.Y. and Ausubel et al., Short Protocols in Molecular Biology (1999) 4th Ed, John Wiley & Sons, Inc. which are incorporated herein by reference) and chemical methods.

Nicotinamide N-methyltransferase (NNMT)

Nicotinamide N-methyltransferase (NNMT) is a cytosolic methyltransferase that catalyzes the methylation of nicotinamide and structurally related pyridines. Specifically, NNMT catalyzes the reaction of S-adenosyl-L-methionine (SAM) with nicotinamide (and structurally related pyridines) yielding S-adenosyl-L-homocysteine (SAH) and N-methylnicotinamide. NNMT is structurally and functionally related to thioether S-methyltransferase and phenylethanolamine N-methyltransferase (Aksoy, S. et al. (1994) *J. Biol. Chem.* 269:14835-14840; Aksoy, S. et al. (1995) *Genomics* 29:555-561). With S-adenosyl-1-methionine as the methyl group donor, the NNMT reaction yields two products: N-methylnicotinamide, which is excreted into urine, and S-adenosyl-1-homocysteine, which is converted into homocysteine by S-adenosyl-1-homocysteine hydrolase (Castro, et al. (2006) *J. Inherit. Metab. Dis.* 29:3-20). NNMT is involved in detoxification reactions of the liver and the regulation of homocysteine (Riederer, M., et al. (2009) *Atherosclerosis* 204:412-417).

As used herein, "nicotinamide N-methyl transferase" or "NNMT" includes any naturally occurring, recombinant, synthetic or semi-synthetic nicotinamide N-methyl transferase protein, or a biologically-active variant or fragment thereof. As used herein, a "biologically-active" NNMT protein, variant or fragment refers to an NNMT protein, or a variant (e.g., an allelic variant, a splice variant) or fragment thereof, which catalyzes the methylation of nicotinamide and structurally related pyridines. One of skill in the art can readily determine whether a candidate NNMT protein, variant or fragment possesses the requisite enzymatic activity using routine assays. Preferably the NNMT protein is a mammalian NNMT protein, more preferably, a human NNMT protein.

The sequence of human NNMT protein (UniProtKB/Swiss-Prot Accession Number P40261) is shown in FIG. 17 (SEQ ID NO:1). The cDNA sequence corresponding to human NNMT mRNA (NCBI Reference Sequence (RefSeq) NM_006169.2) is shown in FIGS. 18A and B (SEQ ID NO:2).

Methods of Treatment

As described herein, it has now been found that NNMT protein is overexpressed in adipose tissue and liver of insulin-resistant mammals. It has further been shown that reducing NNMT expression protects against diet-induced obesity, improves glucose homeostasis and reduces hepatic stress in animal models of insulin resistance (e.g., by using an NNMT antagonist). In particular, as described herein, antisense oligonucleotides that target NNMT mRNA are useful for achieving the above-mentioned effects.

Accordingly, in one aspect, the present invention relates to a method of treating or preventing (e.g., inhibiting) obesity in a subject in need thereof, comprising administering to the subject an NNMT antagonist (e.g., an effective amount of an NNMT antagonist, a therapeutically effective amount of an NNMT antagonist). In another aspect, the invention relates to a method of treating or preventing (e.g., inhibiting) a metabolic disorder (e.g., a metabolic disorder associated with obesity) in a subject in need thereof, comprising administering to the subject an NNMT antagonist (e.g., an effective amount of an NNMT antagonist, a therapeutically effective amount of an NNMT antagonist).

As used herein, the terms "treat," "treating," or "treatment," mean to counteract a medical condition (e.g., obesity, a condition related to obesity) to the extent that the medical condition is improved according to a clinically-acceptable standard. An improvement in a medical condition related to obesity can be determined according to one or more of the following: 1) reduction of body weight, 2) reduction of body mass index (BMI), 3) reduction of waist-to-hip ratio (WHR).

The terms "prevent," "preventing," or "prevention," as used herein, mean reducing the probability/likelihood or risk of obesity or a related condition, or progression by a subject, delaying the onset of a condition related to obesity in the subject, lessening the severity of one or more symptoms of an obesity-related condition in the subject, or any combination thereof. In general, the subject of a preventative regimen most likely will be categorized as being "at-risk", e.g., the risk for the subject developing obesity or a related-condition is higher than the risk for an individual represented by the relevant baseline population.

As used herein, a "subject" refers to a mammal, including primates (e.g., humans), cows, sheep, goats, horses, dogs, cats, rabbits, guinea pigs, rats, mice or other bovine, ovine, equine, canine, feline, rodent or murine species. Examples of suitable subjects include, but are not limited to, human patients (e.g., diabetic, non-diabetic) who are medically overweight or obese, and human patients (e.g., obese, non-obese) who have, or are at risk for developing, insulin resistance or type 2 diabetes. Examples of high-risk groups for the development of insulin resistance or type 2 diabetes include medically overweight and obese individuals.

As used herein, an "effective amount" is an amount sufficient to an amount sufficient to inhibit (e.g., reduce, prevent) production (i.e., expression) or activity of an NNMT protein in a cell or in the bloodstream.

As used herein, a "therapeutically effective amount" is an amount sufficient to achieve the desired therapeutic or prophylactic effect under the conditions of administration, such as an amount sufficient to inhibit (e.g., reduce, prevent) obesity or a related condition (e.g., type 2 diabetes). The effectiveness of a therapy can be determined by one of skill in the art using standard measures and routine methods.

A "condition related to obesity" includes, but is not limited to insulin resistance, type 2 diabetes, hyperglycemia, high blood pressure, high cholesterol, cardiovascular disease, renal disease, cerebrovascular disease, osteoarthritis of weight-bearing joints, sleep apnea, respiratory problems, gastroesophageal reflux, heartburn, depression, infertility, urinary stress incontinence, and menstrual irregularities. Conditions related to obesity occur in individuals who are or have been obese during one or more time periods in life.

The terms "metabolic disorder" or "metabolic disorder associated with obesity" include but are not limited to insulin resistance, type 2 diabetes, impaired glucose tolerance, hyperglycemia, gestational diabetes, dyslipidemia, Metabolic Syndrome, abnormalities in glucose and lipid metabolism, Addison's disease, Celiac disease, Cushing's Syndrome, cystic fibrosis, Fibromyalgia Syndrome, frozen shoulder, Hashimoto's thyroiditis, hemochromatosis, infertility, irritable bowel syndrome, and polycystic ovarian syndrome. Such metabolic disorders can occur in obese/diabetic, obese/non-diabetic, lean/diabetic or lean/non-diabetic individuals.

"Metabolic Syndrome" refers to the co-occurrence in an individual of insulin resistance with multiple conditions selected from obesity (especially central obesity), dyslipidemia (especially high levels of triglycerides and low levels of high density lipoprotein cholesterol), hyperglycemia and/or hypertension. People with Metabolic Syndrome are at increased risk for diabetes and cardiovascular disease, including heart attack, stroke and peripheral vascular disease (Meigs, J. B., *BMJ:* 327, 61-62 (2003)).

The amount of the NNMT antagonist to be administered to a subject (e.g., an effective amount of an NNMT antagonist, a therapeutically effective amount) can be determined by a clinician using the guidance provided herein and other methods known in the art and is dependent on several factors including, for example, the particular agent chosen, the subject's age, sensitivity, tolerance to drugs and overall well-being. For example, suitable dosages for NNMT antagonists that are antibodies can be from about 0.01 mg/kg to about 300 mg/kg body weight per treatment and preferably from about 0.01 mg/kg to about 100 mg/kg, from about 0.01 mg/kg to about 10 mg/kg, from about 1 mg/kg to about 10 mg/kg body weight per treatment. Suitable dosages for a small molecule NNMT antagonist can be from about 0.001 mg/kg to about 100 mg/kg, from about 0.01 mg/kg to about 100 mg/kg, from about 0.01 mg/kg to about 10 mg/kg, from about 0.01 mg/kg to about 1 mg/kg body weight per treatment. Suitable dosages for NNMT antagonists that are proteins or peptides (linear, cyclic, mimetic), will result in a plasma concentration of the peptide from about 0.1 µg/mL to about 200 µg/mL. Suitable dosages for NNMT antisense oligonucleotides can range from about 10 mg to 1000 mg p.o., i.v., or s.c. Determining the dosage for a particular agent, patient and condition is well within the abilities of one skilled in the art. Preferably, the dosage does not cause, or produces minimal, adverse side effects (e.g., immunogenic response, nausea, dizziness, gastric upset, hyperviscosity syndromes, congestive heart failure, stroke, pulmonary edema).

A therapeutically effective amount of an NNMT antagonist can be administered alone, or in combination with one or more other therapeutic agents (e.g., anti-obesity agents, anti-diabetic agents). Suitable agents that are useful for treating obesity and/or related disorders, particularly Type 2 diabetes, which can be administered in combination with NNMT antagonists of the invention, include, but are not limited to, anti-diabetic agents such as insulin, sulfonylureas, meglitinides, biguanides, thiazolidinediones, alpha-glucosidase inhibitors, incretin mimetics, GLP analogs and agonists, GIP analogs, DPP-4 inhibitors, amylin analogues, PPARα/γ ligands, SGLT2 inhibitors, and FBPase inhibitors, and anti-obesity agents such as orlistat, sibutramine, rimonabant, metformin, exenatide, pramlintide and lorcaserin.

The NNMT antagonist can be administered before, after or concurrently with one or more additional therapeutic agents. In some embodiments, the NNMT antagonist and additional therapeutic agent are co-administered simultaneously (e.g., concurrently) as either separate formulations or as a joint formulation. Alternatively, the agents can be administered sequentially, as separate compositions, within an appropriate time frame as determined by the skilled clinician (e.g., a time sufficient to allow an overlap of the pharmaceutical effects of the therapies). The NNMT antagonist and one or more additional therapeutic agents can be administered in a single dose or in multiple doses, in an order and on a schedule suitable to achieve a desired therapeutic effect. Suitable dosages and regimens of administration can be determined by a clinician and are dependent on the agent(s) chosen, pharmaceutical formulation and route of administration, various patient factors and other considerations.

In some embodiments, treatment with an NNMT antagonist may be performed in conjunction with behavioral therapy (e.g., behavioral therapy relating to modifications of diet and physical exercise and stress reduction).

NNMT Antagonists

As defined herein, an "NNMT antagonist" includes any agent that inhibits (e.g., reduces, decreases, eliminates, prevents) the production or activity of an NNMT gene product (e.g., NNMT RNA, NNMT protein). NNMT activities include, but are not limited to, catalyzing the N-methylation of nicotinamide to produce N-methylnicotinamide or catalyzing the N-methylation of other pyridines. In a particular embodiment, an NNMT antagonist inhibits the production, or expression (e.g., transcription, RNA processing, translation), of an NNMT gene or gene product, thereby reducing the level of functional (e.g., biologically active) NNMT protein in a cell (e.g., adipocyte), tissue (e.g., adipose tissue), organ (e.g., liver) or organism. In another embodiment, the NNMT antagonist inhibits an activity of an NNMT gene product by directly binding to the NNMT gene product and interfering with its function. As described further herein, an NNMT antagonist can be, for example, a nucleic acid (e.g., an antisense oligonucleotide, siRNA), an antibody, a small molecule or a peptide.

Nucleic Acid Antagonists

NNMT antagonists include various types of nucleic acids (e.g., antisense oligonucleotides (ASOs), small interfering RNAs (siRNAs), short hairpin RNAs (shRNAs), microRNAs, ribozymes, aptamers). In some embodiments, an NNMT nucleic acid antagonist of the invention inhibits the expression of an NNMT gene or RNA (e.g., hnRNA, mRNA). In a preferred embodiment, a nucleic acid antagonist of NNMT inhibits translation of an NNMT mRNA (e.g., by promoting degradation of the RNA through RNase H-dependent mechanisms). Typically, a nucleic acid antagonist of NNMT will inhibit NNMT expression by hybridizing (e.g., specifically hybridizing) to an NNMT gene or RNA.

Antisense Oligonucleotides (ASOs)

In certain embodiments, the treatment methods of the invention comprise administering antisense oligonucleotides (ASOs) to a subject. Antisense oligonucleotides are generally short single-stranded nucleic acids of about 8 to about 30 nucleotides in length which hybridize to a target nucleic acid sequence (e.g., a portion of an NNMT mRNA) and induce the degradation of the target nucleic acid (e.g., degradation of the RNA through RNase H-dependent mechanisms) or sterically hinder the progression of splicing or translational machinery. (See e.g., Dias N. and Stein C. A., *Mol. Can. Ther.* 1:347-355, 2002).

For example, hybridization may occur between an antisense oligonucleotide and an NNMT nucleic acid described herein (e.g., an NNMT mRNA, SEQ ID NO:2) or a portion thereof. Preferably, an antisense oligonucleotide will hybridize to a portion of a target NNMT nucleic acid that is at least 8 contiguous nucleobases in length. The most common mechanism of hybridization involves hydrogen bonding (e.g., Watson-Crick, Hoogsteen or reversed Hoogsteen hydrogen bonding) between complementary nucleobases of the nucleic acid molecules.

In one embodiment, the antisense oligonucleotides are specifically hybridizable with an NNMT nucleic acid. "Specifically hybridizable" refers to an antisense oligonucleotide that hybridizes to a target nucleic acid to induce a desired effect, while exhibiting minimal or no effects on non-target nucleic acids. Methods of determining whether a sequence is specifically hybridizable to a target nucleic acid are well known in the art.

Hybridization can occur under varying conditions. Stringent conditions are sequence-dependent and are determined by the nature and composition of the nucleic acid molecules to be hybridized. "Stringent hybridization conditions" means conditions under which a nucleic acid molecule, such as an antisense oligonucleotide, will hybridize to a target nucleic acid sequence, but to no or a minimal number of other sequences. Examples of hybridization conditions can be found on pages 2.10.1-2.10.16 (containing Supplements up through Supplement 42) and pages 6.3.1-6 (containing Supplements up through Supplement 24) in *Current Protocols in Molecular Biology* (Ausubel, F. M. et al., eds., containing Supplements up through Supplement 73, January, 2006). Examples of high, medium, and low stringency conditions can be found in the description on page 36, line 1 to page 37, line 12 of WO 98/40404.

Generally, antisense oligonucleotides useful in the present invention are at least 70%, at least 75%, at least 80%, at least 85%, at least 90%, at least 95%, at least 96%, at least 97%, at least 98% or at least 99% complementary to at least a portion (e.g., 8 or more contiguous nucleotides) of an NNMT nucleic acid (e.g., NNMT mRNA, SEQ ID NO:2). The terms "complementary" or "complementarity" refer to the natural binding of the base portions of nucleic acids or nucleic acid mimics under permissive salt and temperature conditions by base-pairing. Complementarity between two single-stranded molecules may be "partial" in which only some of the nucleic acids bind, or it may be complete when total complementarity exists between the single-stranded molecules (that is, when A-T and G-C base pairing is 100% complete). The degree of complementarity between nucleic acid strands has significant effects on the efficiency and strength of hybridization between nucleic acid strands. Percent complementarity of an antisense oligonucleotide with a target nucleic acid can be determined using routine methods.

In a particular embodiment, an antisense oligonucleotide will be fully complementary (i.e., has 100% complementarity) to a target sequence in an NNMT nucleic acid. However, non-complementary nucleobases between an antisense oligonucleotide and an NNMT nucleic acid may be tolerated provided that the antisense compound remains able to specifically hybridize to a target nucleic acid. Moreover, an antisense oligonucleotide may hybridize over one or more segments of an NNMT nucleic acid such that intervening or adjacent segments are not involved in the hybridization event (e.g., a loop structure, mismatch or hairpin structure).

The comparison of nucleotide sequences and determination of percent similarity between two sequences can be accomplished using a mathematical algorithm. (*Computational Molecular Biology*, Lesk, A. M., ed., Oxford University Press, New York, 1988; *Biocomputing: Informatics and Genome Projects*, Smith, D. W., ed., Academic Press, New York, 1993; *Computer Analysis of Sequence Data, Part 1*, Griffin, A. M., and Griffin, H. G., eds., Humana Press, New Jersey, 1994; *Sequence Analysis in Molecular Biology*, von Heinje, G., Academic Press, 1987; and *Sequence Analysis Primer*, Gribskov, M. and Devereaux, J., eds., M. Stockton Press, New York, 1991).

Typically, antisense oligonucleotides will be about 8 to about 30, preferably about 12 to about 21, more preferably about 15 to about 18, nucleobases in length. Thus, an antisense oligonucleotide can be, for example, 8, 9, 10, 11, 12, 13, 14, 15, 16, 17, 18, 19, 20 or 21 nucleobases in length.

Antisense oligonucleotides can include naturally occurring nucleotide subunits (e.g., deoxyribonucleotides, ribonucleotides) and/or nucleotide analogues or mimics. Thus, antisense oligonucleotides can be, for example, DNA, RNA, locked nucleic acid (LNA), peptide nucleic acid (PNA), glycol nucleic acid (GNA), threose nucleic acid (TNA), or morpholino. Preferably, an antisense oligonucleotide comprises RNA.

In addition, the antisense oligonucleotides can be unmodified or modified. An antisense oligonucleotide that is unmodified will include RNA nucleotides or DNA nucleotides comprising naturally occurring nucleobases, sugar moieties and internucleoside linkages. Modified oligonucleotides encompass one or more nucleotides having nucleotide subunits comprising, for example, a modified sugar moiety, modified internucleoside linkage, or modified nucleobase or any combination thereof. Modified antisense compounds are often preferred over native forms because of desirable properties such as, for example, enhanced cellular uptake, enhanced affinity for nucleic acid target, increased stability in the presence of nucleases, or increased inhibitory activity. Chemically modified nucleosides may also be employed to increase the binding affinity of a shortened or truncated antisense oligonucleotide for its target nucleic acid. Consequently, comparable results can often be obtained with shorter antisense compounds that have such chemically modified nucleosides.

In a particular embodiment, an antisense oligonucleotide comprises one or more modified internucleoside linkages. Oligonucleotides having modified internucleoside linkages include internucleoside linkages that retain a phosphorus atom as well as internucleoside linkages that do not have a phosphorus atom. Representative phosphorus-containing internucleoside linkages include, but are not limited to, phosphodiesters, phosphotriesters, methylphosphonates, phosphoramidate, and phosphorothioates. Methods of preparation of phosphorous-containing and non-phosphorous-containing linkages are well known.

In some embodiments, the modified internucleoside linkages in antisense oligonucleotide used in the methods of the invention are phosphorothioate linkages. In other embodiments, each internucleoside linkage of an antisense oligonucleotide is a phosphorothioate internucleoside linkage.

In another embodiment, an antisense oligonucleotide comprises one or more modified sugar moieties. Sugar modifications may impart nuclease stability, binding affinity or some other beneficial biological property to the antisense compounds. The furanosyl sugar ring of a nucleoside can be modified in a number of ways including, but not limited to, addition of a substituent group, particularly at the 2' position; bridging of two non-geminal ring atoms to form a bicyclic nucleic acid (BNA); and substitution of an atom or group such as —S—, —N(R)— or —C($R_1$)($R_2$) for the ring oxygen at the 4'-position. Modified sugars include, but are not limited to: substituted sugars, especially 2'-substituted sugars having a 2'-F, 2'-OCH$_2$ (2'-OMe) or a 2'—O(CH2)$_2$—OCH$_3$(2'-O-methoxyethyl or 2'-MOE) substituent group; and bicyclic modified sugars (BNAs), having a 4'-(CH2)$_n$—O-2' bridge, where n=1 or n=2, including α-L-methyleneoxy (4'-CH2-O-2') BNA, β-D-methyleneoxy (4'-CH2-O-2') BNA and ethyleneoxy (4'-(CH2)$_2$—O-2') BNA. Bicyclic modified sugars also include (6'S)-6' methyl BNA, aminooxy (4'-CH2-O—N(R)-2') BNA, oxyamino (4'-CH2-N(R)—O-2') BNA wherein R is, independently, H, a protecting group or C1-C12 alkyl. The substituent at the 2' position can also be selected from allyl, amino, azido, thio, O-allyl, O—C1-C10 alkyl, OCF$_3$, O(CH$_2$)$_2$SCH$_3$, O(CH$_2$)$_2$—O—N(Rm)(Rn), and O—CH$_2$—

C(=O)—N(Rm)(Rn), where each Rm and Rn is, independently, H or substituted or unsubstituted C1-C10 alkyl. In certain embodiments, such BNA modified nucleotides are high-affinity nucleotides and their incorporation into antisense compounds allows for increased potency and improved therapeutic index. Methods for the preparations of modified sugars are well known to those skilled in the art.

In a particular embodiment, the modified sugar moiety comprises a 2'-O-methoxyethyl (2'-MOE) modification. In a further embodiment, the 2'-MOE modified nucleotides are arranged in a gapmer motif. In a gapmer, an internal position having a plurality of nucleotides that supports RNaseH cleavage is positioned between external regions having a plurality of nucleotides that are chemically distinct from the nucleosides of the internal region. In the case of an antisense oligonucleotide having a gapmer motif, the gap segment generally serves as the substrate for endonuclease cleavage, while the wing segments comprise modified nucleosides. The regions of a gapmer are differentiated by the types of sugar moieties comprising each distinct region. The types of sugar moieties that are used to differentiate the regions of a gapmer may in some embodiments include β-D-ribonucleosides, β-D-deoxyribonucleosides, 2'-modified nucleosides (such 2'-modified nucleosides may include 2'-MOE, and 2'-O—CH3, among others), and bicyclic sugar modified nucleosides (such bicyclic sugar modified nucleosides may include those having a 4'-(CH2)n-O-2' bridge, where n=1 or n=2). In general, each distinct region comprises uniform sugar moieties. The wing-gap-wing motif is frequently described as "X—Y—Z", where "X" represents the length of the 5' wing region, "Y" represents the length of the gap region, and "Z" represents the length of the 3' wing region.

In another embodiment, an antisense oligonucleotide comprises one or more modified nucleobases. Nucleobase (or base) modifications or substitutions are structurally distinguishable from, yet functionally interchangeable with, naturally occurring or synthetic unmodified nucleobases. Both natural and modified nucleobases are capable of participating in hydrogen bonding. Such nucleobase modifications may impart nuclease stability, binding affinity or some other beneficial biological property to antisense compounds. Modified nucleobases include synthetic and natural nucleobases such as, for example, 5-methylcytosine (5-me-C). Certain nucleobase substitutions, including 5-methylcytosine substitutions, are particularly useful for increasing the binding affinity of an antisense compound for a target nucleic acid. For example, 5-methylcytosine substitutions have been shown to increase nucleic acid duplex stability by 0.6-1.2° C. (Sanghvi, Y. S., Crooke, S. T. and Lebleu, B., eds., Antisense Research and Applications, CRC Press, Boca Raton, 1993, pp. 276-278).

In some embodiments, the antisense oligonucleotides comprise at least one modified nucleobase that is a 5-methylcytosine. In further embodiments, each cytosine in the antisense oligonucleotide is a 5-methylcytosine.

Additional nucleobases that may occur in antisense oligonucleotides include 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl (—C≡C—CH$_3$) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine and 3-deazaguanine and 3-deazaadenine.

Heterocyclic base moieties may also include those in which the purine or pyrimidine base is replaced with other heterocycles, for example 7-deazaadenine, 7-deazaguanosine, 2-aminopyridine and 2-pyridone. Nucleobases that are particularly useful for increasing the binding affinity of antisense compounds include 5-substituted pyrimidines, 6-azapyrimidines and N-2, N-6 and O-6 substituted purines, including 2 aminopropyladenine, 5-propynyluracil and 5-propynylcytosine.

Thus, there are a number of different types of antisense oligonucleotides that can be used as NNMT antagonists, including methylphosphonate oligonucleotides, phosphorothioate oligonucleotides, oligonucleotides having a hydrogen at the 2'-position of ribose replaced by an O-alkyl group (e.g., a methyl), polyamide nucleic acid (PNA), phosphorodiamidate morpholino oligomers (deoxyribose moiety is replaced by a morpholine ring), PN (N3'→P5' replacement of the oxygen at the 3' position on ribose by an amine group) and chimeric oligonucleotides (e.g., 2'-O-Methyl/phosphorothioate). Antisense oligonucleotides can be taken up by target cells (e.g., tumor cells) via the process of adsorptive endocytosis. Thus, in the treatment of a subject (e.g., mammalian), antisense NNMT oligonucleotides □ can be delivered to target cells (e.g., tumor cells) by, for example, injection or infusion. For instance, purified oligonucleotides or siRNA/shRNA, can be administered alone or in a formulation with a suitable drug delivery vehicle (e.g., liposomes, cationic polymers, (e.g., poly-L-lysine' PAMAM dendrimers, polyalkylcyanoacrylate nanoparticles and polyethyleneimine) or coupled to a suitable carrier peptide (e.g., homeotic transcription factor, the Antennapedia peptide, Tat protein of HIV-1, E5 CA peptide).

Antisense oligonucleotides can be designed to be specific for a target using predictive algorithms. (See e.g., Ding, Y., and Lawrence, C. E., *Nucleic Acids Res.*, 29:1034-1046, 2001; Sczakiel, G., *Front. Biosci.*, 5:D194-D201, 2000; Scherr, M., et al., *Nucleic Acids Res.*, 28:2455-2461, 2000; Patzel, V., et al. *Nucleic Acids Res.*, 27:4328-4334, 1999; Chiang, M. Y., et al., *J. Biol. Chem.*, 266:18162-18171, 1991; Stull, R. A., et al., *Nucleic Acids Res.*, 20:3501-3508, 1992; Ding, Y., and Lawrence, C. E., *Comput. Chem.*, 23:387-400, 1999; Lloyd, B. H., et al., *Nucleic Acids Res.*, 29:3664-3673, 2001; Mir, K. U., and Southern, E. M., *Nat. Biotechnol.*, 17:788-792, 1999; Sohail, M., et al., *Nucleic Acids Res.*, 29:2041-2051, 2001; Altman, R. K., et al., *J. Comb. Chem.*, 1:493-508, 1999). The antisense oligonucleotides can be produced by suitable methods; for example, nucleic acid (e.g., DNA, RNA, PNA) synthesis using an automated nucleic acid synthesizer (from, e.g., Applied Biosystems) (see also Martin, P., *Helv. Chim. Acta* 78:486-504, 1995). Antisense oligonucleotides can also be stably expressed in a cell containing an appropriate expression vector.

Thus, antisense oligonucleotides for use in the methods of the present invention include naturally occurring, recombinant, synthetic, and semisynthetic. In addition, such compounds can be obtained commercially from a variety of sources (e.g., Isis Pharmaceuticals, Inc., Carlsbad, Calif.).

Other NNMT Nucleic Acid Antagonists

Nucleic acid antagonists of NNMT also include small interfering ribonucleic acids (siRNAs) and short hairpin ribonucleic acids (shRNAs), which are processed into short siRNA-like molecules in a cell, and can prevent the expression (translation) of the NNMT protein (e.g., by promoting degradation of the mRNA encoding the NNMT protein).

siRNA molecules can be polynucleotides that are generally about 20 to about 25 nucleotides long and are designed to bind a specific RNA sequence (e.g., an NNMT mRNA sequence). siRNAs silence gene expression in a sequence-specific manner, binding to a target RNA (e.g., an RNA having the complementary sequence) and causing the RNA to be degraded by endoribonucleases. siRNA molecules able to inhibit the expression of the NNMT gene product can be produced by suitable methods. There are several algorithms that can be used to design siRNA molecules that bind the sequence of a gene of interest (see e.g., Mateeva O. et al. *Nucleic Acids Res.* 35 (8):Epub, 2007; Huesken D. et al., *Nat. Biotechnol.* 23:995-1001; Jagla B. et al., *RNA* 11:864-872, 2005; Shabalinea S. A. *BMC Bioinformatics* 7:65, 2005; Vert J. P. et al. *BMC Bioinformatics* 7:520, 2006). Expression vectors that can stably express siRNA or shRNA are available. (See e.g., Brummelkamp, T. R., *Science* 296: 550-553, 2002, Lee, N S, et al., *Nature Biotechnol.* 20:500-505, 2002; Miyagishi, M., and Taira, K. *Nature Biotechnol.* 20:497-500, 2002; Paddison, P. J., et al., *Genes & Dev.* 16:948-958, 2002; Paul, C. P., et al., *Nature Biotechnol.* 20:505-508; 2002; Sui, G., et al., *Proc. Natl. Acad. Sci. USA* 99(6):5515-5520, 2002; Yu, J-Y, et al., *Proc. Natl. Acad. Sci. USA* 99(9):6047-6052, 2002; Elbashir, S M, et al., *Nature* 411:494-498, 2001.). Stable expression of siRNA/shRNA molecules is advantageous in the treatment of chronic diseases as it enables long-term expression of the molecules, potentially reducing and/or eliminating the need for repeated treatments.

Ribozymes can also be used as NNMT antagonists to inhibit NNMT expression. Ribozymes are RNA molecules possessing enzymatic activity. One class of ribozymes is capable of repeatedly cleaving other separate RNA molecules into two or more pieces in a nucleotide base sequence specific manner. See Kim et al., *Proc Natl Acad Sci USA,* 84:8788 (1987); Haseloff & Gerlach, *Nature,* 334:585 (1988); and Jefferies et al., *Nucleic Acid Res,* 17:1371 (1989). Such ribozymes typically have two functional domains: a catalytic domain and a binding sequence that guides the binding of ribozymes to a target RNA through complementary base-pairing. Once a specifically-designed ribozyme is bound to a target mRNA, it enzymatically cleaves the target mRNA, typically reducing its stability and destroying its ability to directly translate an encoded protein. After a ribozyme has cleaved its RNA target, it is released from that target RNA and thereafter can bind and cleave another target. That is, a single ribozyme molecule can repeatedly bind and cleave new targets.

In accordance with the present invention, a ribozyme may target any portion of the mRNA encoding NNMT. Methods for selecting a ribozyme target sequence and designing and making ribozymes are generally known in the art. See e.g., U.S. Pat. Nos. 4,987,071; 5,496,698; 5,525,468; 5,631,359; 5,646,020; 5,672,511; and 6,140,491, each of which is incorporated herein by reference in its entirety. For example, suitable ribozymes may be designed in various configurations such as hammerhead motifs, hairpin motifs, hepatitis delta virus motifs, group I intron motifs, or RNase P RNA motifs. See e.g., U.S. Pat. Nos. 4,987,071; 5,496,698; 5,525,468; 5,631,359; 5,646,020; 5,672,511; and 6,140,491; Rossi et al., *AIDS Res Human Retroviruses* 8:183 (1992); Hampel & Tritz, *Biochemistry* 28:4929 (1989); Hampel et al., *Nucleic Acids Res,* 18:299 (1990); Perrotta & Been, *Biochemistry* 31:16 (1992); and Guerrier-Takada et al., *Cell,* 35:849 (1983).

Ribozymes can be synthesized by the same methods used for normal RNA synthesis. For example, suitable methods are disclosed in Usman et al., *J Am Chem Soc,* 109:7845-7854 (1987) and Scaringe et al., *Nucleic Acids Res,* 18:5433-5441 (1990). Modified ribozymes may be synthesized by the methods disclosed in, e.g., U.S. Pat. No. 5,652,094; International Publication Nos. WO 91/03162; WO 92/07065 and WO 93/15187; European Patent Application No. 92110298.4; Perrault et al., *Nature,* 344:565 (1990); Pieken et al., *Science,* 253:314 (1991); and Usman & Cedergren, *Trends Biochem Sci,* 17:334 (1992).

Nucleic acid antagonists of NNMT also include nucleic acid molecules (e.g., oligonucleotides) that bind to an NNMT protein and inhibit its activity. Such nucleic acid molecules include aptamers, which are capable of binding to a target molecule of interest (e.g., human NNMT) with high affinity and specificity through interactions other than classic Watson-Crick base pairing (Tuerk and Gold, Science 249:505 (1990); Ellington and Szostak, Nature 346:818 (1990)).

Aptamers, like peptides generated by phage display or monoclonal antibodies (MAbs), are capable of specifically binding to selected targets and, through binding, block their targets' ability to function. Created by an in vitro selection process from pools of random sequence oligonucleotides, aptamers have been generated for over 100 proteins including growth factors, transcription factors, enzymes, immunoglobulins, and receptors. A typical aptamer is 10-15 kDa in size (30-45 nucleotides), binds its target with sub-nanomolar affinity, and discriminates against closely related targets (e.g., will typically not bind other proteins from the same gene family). A series of structural studies have shown that aptamers are capable of using the same types of binding interactions (hydrogen bonding, electrostatic complementarity, hydrophobic contacts, steric exclusion, etc.) that drive affinity and specificity in antibody-antigen complexes.

An aptamer that binds to a target of interest (e.g., a human NNMT protein) can be generated and identified, for example, using a standard process known as "Systematic Evolution of Ligands by Exponential Enrichment" (SELEX), described in, e.g., U.S. Pat. No. 5,475,096 and U.S. Pat. No. 5,270,163.

Antibody Antagonists

An NNMT antagonist also encompasses antibodies that bind (e.g., specifically bind) an NNMT protein. Accordingly, in one embodiment, the invention provides an antibody that binds an NNMT protein (e.g., a human NNMT protein (SEQ ID NO:1)). As used herein, the term "antibody" is intended to encompass both whole antibodies and antibody fragments (e.g., antigen-binding fragments of antibodies, for example, Fv, Fc, Fd, Fab, Fab', F(ab'), and dAb fragments). "Antibody" refers to both polyclonal and monoclonal antibodies and includes naturally-occurring and engineered antibodies. Thus, the term "antibody" includes, for example, human, chimeric, humanized, primatized, veneered, single chain, and domain antibodies (dAbs). (See e.g., Harlow et al., *Antibodies A Laboratory Manual*, Cold Spring Harbor Laboratory, 1988).

Antibodies that bind to an NNMT protein can be produced, constructed, engineered and/or isolated by conventional methods or other suitable techniques. For example, antibodies which are specific for an NNMT protein can be raised against an appropriate immunogen, such as a recombinant mammalian (e.g., human) NNMT protein (e.g., SEQ ID NO:1) or a portion thereof (including synthetic molecules, e.g., synthetic peptides). A variety of such immunization methods have been described (see e.g., Kohler et al., *Nature,* 256: 495-497 (1975) and *Eur. J. Immunol.* 6: 511-519 (1976); Milstein et al., *Nature* 266: 550-552 (1977); Koprowski et al., U.S. Pat. No. 4,172,124; Harlow, E. and D. Lane, 1988, *Antibodies: A Laboratory Manual*, (Cold Spring Harbor Laboratory: Cold Spring Harbor, N.Y.); *Current Protocols In Molecular Biology*, Vol. 2 (Supplement 27, Summer '94), Ausubel, F. M. et al., Eds., (John Wiley & Sons: New York, N.Y.), Chapter 11, (1991)). Antibodies can also be raised by immunizing a suitable host (e.g., mouse) with cells that express NNMT (e.g., adipocyte cells/cell lines) or cells engineered to express NNMT (e.g., transfected cells). (See e.g., Chuntharapai et al., *J. Immunol.*, 152:1783-1789 (1994); Chuntharapai et al. U.S. Pat. No. 5,440,021).

At an appropriate time after immunization, e.g., when the antibody titers are highest, antibody-producing cells can be obtained from the immunized animal and used to prepare monoclonal antibodies by standard techniques, such as the hybridoma technique originally described by Kohler and Milstein (*Nature* 256:495-497, 1975), the human B cell hybridoma technique (Kozbor et al., *Immunol. Today* 4:72, 1983), the EBV-hybridoma technique (Cole et al., Monoclonal Antibodies and Cancer Therapy, Alan R. Liss, Inc., pp. 77-96, 1985) or trioma techniques. The technology for producing hybridomas is well known (see generally Current Protocols in Immunology, Coligan et al., (eds.) John Wiley & Sons, Inc., New York, N.Y., 1994). Briefly, an immortal cell line (typically a myeloma) is fused to lymphocytes (typically splenocytes) from a mammal immunized with an immunogen as described above, and the culture supernatants of the resulting hybridoma cells are screened to identify a hybridoma producing a monoclonal antibody that binds a polypeptide described herein.

Any of the many well known protocols used for fusing lymphocytes and immortalized cell lines can be applied for the purpose of generating a monoclonal antibody to a polypeptide of the invention (see, e.g., Current Protocols in Immunology, supra; Galfre et al., *Nature*, 266:55052, 1977; R. H. Kenneth, in Monoclonal Antibodies: A New Dimension In Biological Analyses, Plenum Publishing Corp., New York, N.Y., 1980; and Lerner, *Yale J. Biol. Med.* 54:387-402, 1981). Moreover, the ordinarily skilled worker will appreciate that there are many variations of such methods that also would be useful.

In one alternative to preparing monoclonal antibody-secreting hybridomas, a monoclonal antibody to an NNMT protein can be identified and isolated by screening a recombinant combinatorial immunoglobulin library (e.g., an antibody phage display library) with the target polypeptide to thereby isolate immunoglobulin library members that bind the polypeptide. Kits for generating and screening phage display libraries are commercially available (e.g., the Pharmacia Recombinant Phage Antibody System, Catalog No. 27-9400-01; and the Stratagene SurfZAP™ Phage Display Kit, Catalog No. 240612). Additionally, examples of methods and reagents particularly amenable for use in generating and screening antibody display libraries can be found in, for example, U.S. Pat. No. 5,223,409; PCT Publication No. WO 92/18619; PCT Publication No. WO 91/17271; PCT Publication No. WO 92/20791; PCT Publication No. WO 92/15679; PCT Publication No. WO 93/01288; PCT Publication No. WO 92/01047; PCT Publication No. WO 92/09690; PCT Publication No. WO 90/02809; Fuchs et al., *Bio/Technology* 9:1370-1372, 1991; Hay et al., *Hum. Antibodies Hybridomas* 3:81-85, 1992; Huse et al., *Science* 246: 1275-1281, 1989; and Griffiths et al., *EMBO J.* 12:725-734, 1993.

Antibody fragments (e.g., antigen-binding fragments) can be produced by enzymatic cleavage or by recombinant techniques. For example, papain or pepsin cleavage can generate Fab or F(ab')$_2$ fragments, respectively. Other proteases with the requisite substrate specificity can also be used to generate Fab or F(ab')$_2$ fragments.

Antibodies can also be produced in a variety of truncated forms using antibody genes in which one or more stop codons has been introduced upstream of the natural stop site. For example, a chimeric gene encoding a F(ab')$_2$ heavy chain portion can be designed to include DNA sequences encoding the CH$_1$ domain and hinge region of the heavy chain.

Single chain, human, chimeric, humanized, primatized (CDR-grafted), or veneered antibodies comprising portions derived from different species, are also encompassed by the present invention and the term "antibody". The various portions of these antibodies can be joined together chemically by conventional techniques, or can be prepared as a contiguous protein using genetic engineering techniques. For example, nucleic acids encoding a chimeric or humanized chain can be expressed to produce a contiguous protein. See, e.g., Cabilly et al., U.S. Pat. No. 4,816,567; Cabilly et al., European Patent No. 0,125,023 B1; Boss et al., U.S. Pat. No. 4,816,397; Boss et al., European Patent No. 0,120,694 B1; Neuberger, M. S. et al., WO 86/01533; Neuberger, M. S. et al., European Patent No. 0,194,276 B1; Winter, U.S. Pat. No. 5,225,539; Winter, European Patent No. 0,239,400 B1; Queen et al., European Patent No. 0 451 216 B1; and Padlan, E. A. et al., EP 0 519 596 A1. See also, Newman, R. et al., *BioTechnology,* 10: 1455-1460 (1992), regarding primatized antibody, and Ladner et al., U.S. Pat. No. 4,946,778 and Bird, R. E. et al., *Science,* 242: 423-426 (1988)) regarding single chain antibodies.

Humanized antibodies can be produced using synthetic or recombinant DNA technology using standard methods or other suitable techniques. Nucleic acid (e.g., cDNA) sequences coding for humanized variable regions can also be constructed using PCR mutagenesis methods to alter DNA sequences encoding a human or humanized chain, such as a DNA template from a previously humanized variable region (see e.g., Kamman, M., et al., *Nucl. Acids Res.,* 17: 5404 (1989)); Sato, K., et al., *Cancer Research,* 53: 851-856 (1993); Daugherty, B. L. et al., *Nucleic Acids Res.,* 19(9): 2471-2476 (1991); and Lewis, A. P. and J. S. Crowe, *Gene,* 101: 297-302 (1991)). Using these or other suitable methods, variants can also be readily produced. In one embodiment, cloned variable regions (e.g., dAbs) can be mutated, and sequences encoding variants with the desired specificity can be selected (e.g., from a phage library; see e.g., Krebber et al., U.S. Pat. No. 5,514,548; Hoogenboom et al., WO 93/06213, published Apr. 1, 1993).

Other suitable methods of producing or isolating antibodies of the requisite specificity can be used, including, for example, methods which select a recombinant antibody or antibody-binding fragment (e.g., dAbs) from a library (e.g., a phage display library), or which rely upon immunization of transgenic animals (e.g., mice). Transgenic animals capable of producing a repertoire of human antibodies are well-known in the art (e.g., Xenomouse® (Abgenix, Fremont, Calif.)) and can be produced using suitable methods (see e.g., Jakobovits et al., *Proc. Natl. Acad. Sci. USA,* 90: 2551-2555 (1993); Jakobovits et al., *Nature,* 362: 255-258 (1993); Lonberg et al., U.S. Pat. No. 5,545,806; Surani et al., U.S. Pat. No. 5,545,807; Lonberg et al., WO 97/13852).

Once produced, an antibody specific for NNMT can be readily identified using methods for screening and isolating specific antibodies that are well known in the art. See, for example, Paul (ed.), Fundamental Immunology, Raven Press, 1993; Getzoff et al., Adv. in Immunol. 43:1-98, 1988; Goding (ed.), Monoclonal Antibodies: Principles and Practice, Academic Press Ltd., 1996; Benjamin et al., Ann. Rev. Immunol. 2:67-101, 1984. A variety of assays can be utilized to detect antibodies that specifically bind to NNMT proteins. Exemplary assays are described in detail in Antibodies: A Laboratory Manual, Harlow and Lane (Eds.), Cold Spring Harbor Laboratory Press, 1988. Representative examples of such assays include: concurrent immunoelectrophoresis, radioimmunoassay, radioimmuno-precipitation, enzyme-linked immunosorbent assay (ELISA), dot blot or Western blot assays, inhibition or competition assays, and sandwich assays.

In certain embodiments, the antibodies have a high binding affinity for NNMT. Such antibodies will preferably have an affinity (e.g., binding affinity) for NNMT, expressed as $K_d$, of at least about $10^{-7}$ M, such as about $0.4 \times 10^{-7}$ M or about $0.6 \times 10^{-7}$ M, or higher, for example, at least about $10^{-8}$ M, at least about $10^{-9}$ M, or at least about $10^{-10}$ M. The binding affinity of an antibody can be readily determined by one of ordinary skill in the art, for example, by Scatchard analysis (Scatchard, G., Ann. NY Acad. Sci. 51: 660-672, 1949). Binding affinity can also be determined using a commercially available biosensor instrument (BIACORE, Pharmacia Biosensor, Piscataway, N.J.), wherein protein is immobilized onto the surface of a receptor chip. See, Karlsson, J. Immunol. Methods 145:229-240, 1991 and Cunningham and Wells, J. Mol. Biol. 234:554-563, 1993. This system allows the determination of on- and off-rates, from which binding affinity can be calculated, and assessment of stoichiometry of binding.

Suitable antibodies can further include a label, such as, for example, a detectable label that permits detection of the antibody, and proteins bound by the antibody (e.g., NNMT), in a biological sample. A detectable label is particularly suitable for diagnostic applications. For example, an NNMT antibody can be labeled with a radioactive isotope (radioisotope), which can be detected by one of skill in the art using a gamma counter, a scintillation counter or by autoradiography or other suitable means. Isotopes which are useful for the purpose of the present invention include, but are not limited to: $^{3}H$, $^{125}I$, $^{131}I$, $^{32}P$, $^{35}S$, $^{14}C$, $^{51}Cr$, $^{36}Cl$, $^{57}Co$, $^{58}CO$, $^{59}Fe$ and $^{75}Se$.

Antibodies can also be labeled with a fluorescent compound (e.g., dyes). When the fluorescently labeled antibody is exposed to light of the proper wave length, its presence can then be detected due to the fluorescence of the compound. Among the most commonly used fluorescent labels are fluorescein isothiocyanate, rhodamine, phycoerytherin, phycocyanin, allophycocyanin, o-phthaldehyde and fluorescamine. the antibodies of the invention can also be labeled using fluorescence emitting metals such as $^{152}Eu$, or others of the lanthanide series. These metals can be attached to the antibody molecule using such metal chelating groups as diethylenetriaminepentaacetic acid (DTPA), tetraaza-cyclododecane-tetraacetic acid (DOTA) or ethylenediaminetetraacetic acid (EDTA).

Antibodies useful in the present invention can be coupled to a chemiluminescent compound. Examples of useful chemiluminescent labeling compounds are luminol, isoluminol, theromatic acridinium ester, imidazole, acridinium salt and oxalate ester.

Likewise, a bioluminescent compound may be used to label the antibody of the present invention. Bioluminescence is a type of chemiluminescence found in biological systems in which a catalytic protein increases the efficiency of the chemiluminescent reaction. The presence of a bioluminescent protein is determined by detecting the presence of luminescence. Useful bioluminescent compounds for purposes of labeling antibodies are luciferin, luciferase and aequorin.

Detection of the labeled antibodies can be accomplished by a scintillation counter, for example, if the detectable label is a radioactive gamma emitter, or by a fluorometer, for example, if the label is a fluorescent material. In the case of an enzyme label, the detection can be accomplished by colorimetric methods which employ a substrate for the enzyme. Detection may also be accomplished by visual comparison of the extent of the enzymatic reaction of a substrate to similarly prepared standards.

Accordingly, the antibodies described herein can also be used as a stain for tissue sections. For example, a labeled antibody that binds to NNMT can be contacted with a tissue sample, e.g., an adipose tissue section, a liver tissue biopsy). This section may then be washed and the label detected using an appropriate means.

Antibodies used for therapeutic purposes may include a cytotoxic agent that is capable of selectively killing cells that express NNMT. For example, bacterial toxins such as diphtheria toxin, or ricin can be used. Methods for producing antibodies comprising fragment A of diphtheria toxin are taught in U.S. Pat. No. 4,675,382 (1987). Diphtheria toxin contains two polypeptide chains. The B chain binds the toxin to a receptor on a cell surface. The A chain actually enters the cytoplasm and inhibits protein synthesis by inactivating elongation factor 2, the factor that translocates ribosomes along mRNA concomitant with hydrolysis of ETP. See Darnell, J. et al., in Molecular Cell Biology, Scientific American Books, Inc., page 662 (1986). Alternatively, an antibody comprising ricin, a toxic lectin, may be prepared. Other suitable cytotoxic agents are know by those of skill in the art.

Small Molecule Antagonists

NNMT antagonists can also be small molecules. Examples of small molecules include organic compounds, organometallic compounds, inorganic compounds, and salts of organic, organometallic or inorganic compounds. Atoms in a small molecule are typically linked together via covalent and/or ionic bonds. The arrangement of atoms in a small organic molecule may represent a chain (e.g. a carbon-carbon chain or a carbon-heteroatom chain), or may represent a ring containing carbon atoms, e.g. benzene or a policyclic system, or a combination of carbon and heteroatoms, i.e., heterocycles such as a pyrimidine or quinazoline. Although small molecules can have any molecular weight, they generally include molecules that are less than about 5,000 daltons. For example, such small molecules can be less than about 1000 daltons and, preferably, are less than about 750 daltons or, more preferably, are less than about 500 daltons. Small molecules and other non-peptidic NNMT antagonists can be found in nature (e.g., identified, isolated, purified) and/or produced synthetically (e.g., by traditional organic synthesis, bio-mediated synthesis, or a combination thereof). See e.g. Ganesan, Drug Discov. Today 7(1): 47-55 (January 2002); Lou, Drug Discov. Today, 6(24): 1288-1294 (December 2001). Examples of naturally occurring small molecules include, but are not limited to, hormones, neurotransmitters, nucleotides, amino acids, sugars, lipids, and their derivatives.

Peptide Antagonists

An NNMT antagonist can also be a peptide (e.g., a peptide that binds to an NNMT protein). The peptide can comprise any suitable L- and/or D-amino acid, for example, common α-amino acids (e.g., alanine, glycine, valine), non-α-amino acids (e.g., β-alanine, 4-aminobutyric acid, 6-aminocaproic acid, sarcosine, statine), and unusual amino acids (e.g., citrulline, homocitruline, homoserine, norleucine, norvaline, ornithine). The amino, carboxyl and/or other functional groups on a peptide can be free (e.g., unmodified) or protected with a suitable protecting group. Suitable protecting groups for amino and carboxyl groups, and methods for adding or removing protecting groups are known in the art and are disclosed in, for example, Green and Wuts, "*Protecting Groups in Organic Synthesis*", John Wiley and Sons, 1991.

The functional groups of a peptide can also be derivatized (e.g., alkylated) using art-known methods.

The peptide NNMT antagonist can comprise one or more modifications (e.g., amino acid linkers, acylation, acetylation, amidation, methylation, terminal modifiers (e.g., cyclizing modifications)), if desired. The peptide can also contain chemical modifications (e.g., N-methyl-α-amino group substitution). In addition, the peptide antagonist can be an analog of a known and/or naturally-occurring peptide, for example, a peptide analog having conservative amino acid residue substitution(s). These modifications can improve various properties of the peptide (e.g., solubility, binding), including its NNMT antagonist activity.

Peptide antagonists can be linear, branched or cyclic, e.g., a peptide having a heteroatom ring structure that includes several amide bonds. In a particular embodiment, the peptide is a cyclic peptide. Such peptides can be produced by one of skill in the art using standard techniques. For example, a peptide can be derived or removed from a native protein by enzymatic or chemical cleavage, or can be synthesized by suitable methods, for example, solid phase peptide synthesis (e.g., Merrifield-type synthesis) (see, e.g., Bodanszky et al. "*Peptide Synthesis,*" John Wiley & Sons, Second Edition, 1976). Peptides that are NNMT antagonists can also be produced, for example, using recombinant DNA methodologies or other suitable methods (see, e.g., Sambrook J. and Russell D. W., *Molecular Cloning: A Laboratory Manual,* $3^{rd}$ Edition, Cold Spring Harbor Laboratory Press, Cold Spring Harbor, N.Y., 2001).

Peptides can be synthesized and assembled into libraries comprising a few to many discrete molecular species. Such libraries can be prepared using methods of combinatorial chemistry, and can be screened using any suitable method to determine if the library comprises peptides with a desired biological activity. Such peptide antagonists can then be isolated using suitable methods known by those of skill in the art.

Peptidomimetic Antagonists

NNMT antagonists can also be peptidomimetics. For example, polysaccharides can be prepared that have the same functional groups as peptides. Peptidomimetics can be designed, for example, by establishing the three dimensional structure of a peptide agent in the environment in which it is bound or will bind to a target molecule. The peptidomimetic comprises at least two components, the binding moiety or moieties and the backbone or supporting structure.

The binding moieties are the chemical atoms or groups which will react or form a complex (e.g., through hydrophobic or ionic interactions) with a target molecule, for instance, human NNMT. For example, the binding moieties in a peptidomimetic can be the same as those in a peptide or protein antagonist. The binding moieties can be an atom or chemical group which reacts with the receptor in the same or similar manner as the binding moiety in the peptide antagonist. For example, computational chemistry can be used to design peptide mimetics of peptides that bind NNMT proteins. Examples of binding moieties suitable for use in designing a peptidomimetic for a basic amino acid in a peptide include nitrogen containing groups, such as amines, ammoniums, guanidines and amides or phosphoniums. Examples of binding moieties suitable for use in designing a peptidomimetic for an acidic amino acid include, for example, carboxyl, lower alkyl carboxylic acid ester, sulfonic acid, a lower alkyl sulfonic acid ester or a phosphorous acid or ester thereof.

The supporting structure is the chemical entity that, when bound to the binding moiety or moieties, provides the three dimensional configuration of the peptidomimetic. The supporting structure can be organic or inorganic. Examples of organic supporting structures include polysaccharides, polymers or oligomers of organic synthetic polymers (such as, polyvinyl alcohol or polylactide). It is preferred that the supporting structure possess substantially the same size and dimensions as the peptide backbone or supporting structure. This can be determined by calculating or measuring the size of the atoms and bonds of the peptide and peptidomimetic. In one embodiment, the nitrogen of the peptide bond can be substituted with oxygen or sulfur, for example, forming a polyester backbone. In another embodiment, the carbonyl can be substituted with a sulfonyl group or sulfinyl group, thereby forming a polyamide (e.g., a polysulfonamide). Reverse amides of the peptide can be made (e.g., substituting one or more -CONH- groups for a -NHCO- group). In yet another embodiment, the peptide backbone can be substituted with a polysilane backbone.

These compounds can be manufactured by known methods. For example, a polyester peptidomimetic can be prepared by substituting a hydroxyl group for the corresponding α-amino group on amino acids, thereby preparing a hydroxyacid and sequentially esterifying the hydroxyacids, optionally blocking the basic and acidic side chains to minimize side reactions. Determining an appropriate chemical synthesis route can generally be readily identified upon determining the chemical structure.

Peptidomimetics can be synthesized and assembled into libraries comprising a few to many discrete molecular species. Such libraries can be prepared using well-known methods of combinatorial chemistry, and can be screened to determine if the library comprises one or more peptidomimetics which have the desired activity. Such peptidomimetic antagonists can then be isolated by suitable methods.

Identification of NNMT Antagonists/Screening Methods

In another aspect, the invention relates to a method of identifying a compound useful for treating obesity or a related condition (e.g., a metabolic condition described herein). NNMT antagonists (e.g., NNMT antagonists having binding specificity for an NNMT gene product) can be identified in a screen, for example, a high-throughput screen of chemical compounds and/or libraries (e.g., chemical, peptide, nucleic acid libraries).

Antibodies that specifically bind human NNMT can be identified, for example, by screening commercially available combinatorial antibody libraries (Dyax Corp., MorphoSys AG). Suitable combinatorial antibody libraries and standard methods of screening these libraries are described in Hoet et al., *Nature Biotechnology* 23(3):344-348 (2005) and Rauchenberger et al., *J. Biol. Chem.* 278(40):38194-38205 (2003), the contents of which are incorporated herein by reference. Such libraries or collections of molecules can also be prepared using well-known chemical methods.

Alternatively murine antibodies that specifically bind human NNMT can be identified, for example, by immunizing mice with NNMT proteins, protein fragments or peptides, along with an adjuvant to break tolerance to the antigen. These antibodies can be screened for the desired specificity and activity and then humanized using known techniques to create suitable agents for the treatment of human disease.

Compounds or small molecules can be identified from numerous available libraries of chemical compounds from, for example, the Chemical Repository of the National Cancer Institute and the Molecular Libraries Small Molecules Repository (PubChem), as well as libraries of the Institute of Chemistry and Cell Biology at Harvard University and other libraries that are available from commercial sources (e.g., Chembridge, Peakdale, CEREP, MayBridge, Bionet). Such libraries or collections of molecules can also be prepared using well-known chemical methods, such as well-known methods of combinatorial chemistry. The libraries can be screened to identify compounds that bind and inhibit NNMT.

Identified compounds can serve as lead compounds for further diversification using well-known methods of medicinal chemistry. For example, a collection of compounds that are structural variants of the lead can be prepared and screened for NNMT binding and/or inhibitory activity. This can result in the development of a structure activity relationship that links the structure of the compounds to biological activity. Compounds that have suitable binding and inhibitory activity can be developed further for in vivo use.

Agents that bind NNMT can be evaluated further for NNMT antagonist activity. For example, a composition comprising an NNMT protein can be used in a screen or binding assay to detect and/or identify agents that bind and antagonize the NNMT protein. Compositions suitable for use include, for example, cells that naturally express an NNMT protein (e.g., adipocytes, hepatocytes), extracts of such cells, and recombinant NNMT protein.

An agent that binds an NNMT protein can be identified in a competitive binding assay, for example, in which the ability of a test agent to inhibit the binding of NNMT to a reference agent is assessed. The reference agent can be a full-length NNMT protein or a portion thereof. The reference agent can be labeled with a suitable label (e.g., radioisotope, epitope label, affinity label (e.g., biotin and avidin or streptavidin), spin label, enzyme, fluorescent group, chemiluminescent group, dye, metal (e.g., gold, silver), magnetic bead) and the amount of labeled reference agent required to saturate the NNMT protein in the assay can be determined. The specificity of the formation of the complex between the NNMT protein and the test agent can be determined using a suitable control (e.g., unlabeled agent, label alone).

The capacity of a test agent to inhibit formation of a complex between the reference agent and an NNMT protein can be determined as the concentration of test agent required for 50% inhibition ($IC_{50}$ value) of specific binding of labeled reference agent. Specific binding is preferably defined as the total binding (e.g., total label in complex) minus the non-specific binding. Non-specific binding is preferably defined as the amount of label still detected in complexes formed in the presence of excess unlabeled reference agent. Reference agents suitable for use in the method include molecules and compounds which specifically bind to NNMT, e.g., an antibody that binds NNMT.

An agent that antagonizes an NNMT protein can be identified by screening for agents that have an ability to antagonize (reduce, prevent, inhibit) one or more activities of NNMT, such as, for example, catalyzing the methylation of nicotinamide or a structurally related pyridine. Such activities can be assessed by one of skill in the art using any appropriate in vitro or in vivo assay.

In a particular embodiment, the invention relates to a method of identifying a compound useful for treating obesity or a related condition. The method comprises the steps of administering a test compound to a non-human animal (e.g., a non-human mammal), determining the expression or activity of NNMT in the animal following administration of the compound, and selecting a compound that inhibits the expression or activity of NNMT in the animal that has been administered the test compound relative to a control non-human animal that was not administered the test compound. A decrease in the expression or activity of NNMT in the animal that has been administered the test compound relative to a control non-human animal that was not administered the test compound indicates the test compound is useful for treating obesity or a related condition. In a particular embodiment, the test compound is an antisense oligonucleotide.

In another embodiment, the screening method of the invention comprises the steps of providing a test compound to a sample (e.g., a cell sample, a tissue sample), determining the expression or activity of NNMT in the sample after the test compounded has been provided, and selecting a test compound that inhibits the expression or activity of NNMT in the sample relative to a suitable control (e.g., a sample that was not provided with the test compound). A decrease in the expression or activity of NNMT in the sample to which the test compound was provided relative to the control sample indicates the test compound is useful for treating obesity or a related condition.

The sample can be, for example, a cell sample (e.g., a sample comprising adipocytes, a sample comprising hepatocytes) a tissue sample (e.g., an adipose tissue sample, a liver tissue sample), or a whole blood, plasma, serum or urine sample.

Compounds suitable for use in the screening methods of the invention include any of the classes of NNMT antagonists described herein. In a particular embodiment, the test compound is an antisense oligonucleotide.

Pharmaceutical Compositions

An NNMT antagonist can be administered to a mammalian subject in a pharmaceutical or physiological composition, for example, as part of a pharmaceutical composition comprising an NNMT antagonist and a pharmaceutically acceptable carrier. Formulations or compositions (e.g., solution, emulsion or capsule) comprising an NNMT antagonist (e.g., an NNMT antisense oligonucleotide) or compositions comprising an NNMT antagonist and one or more other therapeutic agents (e.g., an anti-diabetic agent) will vary according to the route of administration selected. Suitable pharmaceutical carriers can contain inert ingredients which do not interact with the NNMT antagonist. Standard pharmaceutical formulation techniques can be employed, such as those described in Remington's Pharmaceutical Sciences, Mack Publishing Company, Easton, Pa. Suitable pharmaceutical carriers for parenteral administration include, for example, sterile water, physiological saline, bacteriostatic saline (saline containing about 0.9% mg/ml benzyl alcohol), phosphate-buffered saline, Hank's solution, Ringer's lactate and the like. Formulations can also include small amounts of substances that enhance the effectiveness of the active ingredient (e.g., emulsifying, solubilizing, pH buffering, wetting agents). Methods of encapsulation compositions (such as in a coating of hard gelatin or cyclodextran) are known in the art. For inhalation, the agent can be solubilized and loaded into a suitable dispenser for administration (e.g., an atomizer or nebulizer or pressurized aerosol dispenser).

Modes of Administration

An NNMT antagonist may be administered to a subject by a variety of routes, preferably in the form of a pharmaceutical composition adapted to a desired route. The preferred route will depend, in part, on the condition being treated. The compounds and compositions may, for example, be administered intravascularly, intramuscularly, subcutaneously, intraperitoneally, orally or topically. It will be obvious to those skilled in the art that the following dosage forms may comprise as the active ingredient, either compounds or a corresponding pharmaceutically acceptable salt of a compound. Preferred routes of administration for the NNMT antagonists include oral, intravenous and subcutaneous administration.

For oral administration, the pharmaceutical compositions comprising an NNMT antagonist may be in the form of, for example, a tablet, capsule, suspension or liquid. The composition is preferably made in the form of a dosage unit containing a therapeutically effective amount of the active ingredient. Examples of such dosage units are tablets and capsules. For therapeutic purposes, the tablets and capsules can contain, in addition to the active ingredient, conventional carriers such as binding agents, for example, acacia gum, gelatin, polyvinylpyrrolidone, sorbitol, or tragacanth; fillers, for example, calcium phosphate, glycine, lactose, maize-starch, sorbitol, or sucrose; lubricants, for example, magnesium stearate, polyethylene glycol, silica, or talc; disintegrants, for example potato starch, flavoring or coloring agents, or acceptable wetting agents. Oral liquid preparations generally in the form of aqueous or oily solutions, suspensions, emulsions, syrups or elixirs may contain conventional additives such as suspending agents, emulsifying agents, non-aqueous agents, preservatives, coloring agents and flavoring agents. Examples of additives for liquid preparations include acacia, almond oil, ethyl alcohol, fractionated coconut oil, gelatin, glucose syrup, glycerin, hydrogenated edible fats, lecithin, methyl cellulose, methyl or propyl para-hydroxybenzoate, propylene glycol, sorbitol, or sorbic acid.

In some embodiments, an NNMT antagonist may be administered parenterally, via injection. Parenteral administration can include, for example, intraarticular, intramuscular, intravenous, intraventricular, intraarterial, intrathecal, subcutaneous, or intraperitoneal administration. Formulations for parenteral administration may be in the form of aqueous or non-aqueous isotonic sterile injection solutions or suspensions. These solutions or suspensions may be prepared from sterile powders or granules having one or more of the carriers mentioned for use in the formulations for oral administration. The compounds may be dissolved in polyethylene glycol, propylene glycol, ethanol, corn oil, benzyl alcohol, sodium chloride, and/or various buffers (e.g., sodium bicarbonate, sodium hydroxide).

The compounds of the present invention may also be prepared in suitable forms to be applied using a transdermal patch, resulting in absorption of the compound into the bloodstream through the skin. Exemplary types of transdermal patches are known in the art and include single-layer drug-in adhesive patches, multi-layer drug-in adhesive patches, reservoir patches, matrix patches and vapour patches.

For rectal administration, an NNMT antagonist may be administered in the form of suppositories admixed with conventional carriers such as cocoa butter, wax or other glyceride. For preparing suppositories, a low-melting wax, such as a mixture of fatty acid glycerides or cocoa butter, is first-melted and the active ingredient is dispersed homogeneously therein, as by stirring. The molten homogeneous mixture is then poured into convenient sized molds, allowed to cool, and thereby to solidify.

Delivery can also be by injection into the brain or body cavity of a patient or by use of a timed release or sustained release matrix delivery systems, or by onsite delivery using micelles, gels and liposomes. Nebulizing devices, powder inhalers, and aerosolized solutions are representative of methods that may be used to administer such preparations to the respiratory tract. Delivery can be in vitro, in vivo, or ex vivo.

In some embodiments, an NNMT antagonist can be administered via in vivo expression. In vivo expression can be accomplished by somatic cell expression according to suitable methods (see, e.g., U.S. Pat. No. 5,399,346). In addition, a nucleic acid encoding an NNMT antagonist, such as a peptide or nucleic antisense oligonucleotide, may be provided to a cell or administered to a subject so as to stimulate production of the NNMT antagonist in vivo. For this purpose, various techniques and reagents have been developed. For example, a number of viral vectors have been developed that allow for transfection and, in some cases, integration of the virus into the host (e.g., cell or subject). See, for example, Dubensky et al. (1984) Proc. Natl. Acad. Sci. USA 81, 7529-7533; Kaneda et al., (1989) Science 243, 375-378; Hiebert et al. (1989) Proc. Natl. Acad. Sci. USA 86, 3594-3598; Hatzoglu et al. (1990) J. Biol. Chem. 265, 17285-17293 and Ferry, et al. (1991) Proc. Natl. Acad. Sci. USA 88, 8377-8381. The vector may be administered by injection, e.g. intravascularly or intramuscularly, inhalation, or another parenteral mode. Non-viral delivery methods such as administration of the DNA via complexes with liposomes, or by injection, catheter or biolistics, may also be used.

Any suitable means for introducing polynucleotides into cells or mammals (human or non-human) may be adapted to the practice of this invention for the delivery of various nucleic acid constructs into the intended recipient (e.g., a host cell or a host subject). Gene transfer methodologies can be employed to transfer a coding sequence for an NNMT antagonist, or an analog thereof, to a subject such that the gene can be replicated and expressed in vivo. Particularly useful gene therapy methods are discussed in the published international application WO 93/00051, which is incorporated herein by reference.

In one embodiment of the invention, the nucleic acid constructs are delivered to cells by transfection, for example, by delivery of a "naked" nucleic acid or a nucleic acid that is complexed with a colloidal dispersion system. A colloidal system includes macromolecule complexes, nanocapsules, microspheres, beads, and lipid-based systems including oil-in-water emulsions, micelles, mixed micelles, and liposomes. An exemplary colloidal system of this invention is a lipid-complexed or liposome-formulated DNA. In the former approach, prior to formulation of DNA, e.g., with lipid, a plasmid containing a transgene bearing the desired DNA constructs may first be optimized for expression (e.g., inclusion of an intron in the 5' untranslated region and elimination of unnecessary sequences (Felgner, et al, Ann NY Acad Sci 126-139, 1995). Formulation of DNA, e.g. with various lipid or liposome materials, may then be accomplished using known methods and materials and delivered to the recipient mammal. See, e.g., Canonico et al, Am J Respir Cell Mol Biol 10:24-29, 1994; Tsan et al, Am J Physiol 268; Alton et al., Nat. Genet. 5:135-142, 1993 and U.S. Pat. No. 5,679,647 by Carson et al.

Further, a nucleic acid encoding an NNMT antagonist can also be incorporated into retroviral, adenoviral or other suitable vectors (preferably, a replication deficient infectious vector or recombinant bacterial or eukaryotic plasmids) for delivery, or can be introduced into a transfected or transformed host cell capable of expressing the peptide for delivery. In the latter embodiment, the cells can be implanted (alone or in a barrier device), injected or otherwise introduced in an amount effective to express the polypeptide in a therapeutically effective amount.

In a particular embodiment, an NNMT antagonist is administered to a subject via a viral vector that expresses a nucleic molecule encoding the NNMT antagonist. For example, a transgene may be incorporated into any of a variety of viral vectors useful in gene therapy including, but not limited to, recombinant retroviruses (e.g., lentiviral vectors), adenovirus, adeno-associated virus (AAV), herpes simplex derived vectors, hybrid adeno-associated/herpes simplex viral vectors, influenza viral vectors (e.g., vectors based on the influenza A virus), and alphaviruses, for example the Sinbis and semliki forest viruses.

Alternatively, an NNMT antagonist can be administered to a subject in conjunction with a delivery reagent. Suitable delivery reagents for administration of the NNMT antagonists include the Mirus Transit TKO lipophilic reagent; lipofectin; lipofectamine; cellfectin; or polycations (e.g., polylysine), or liposomes.

In a particular embodiment, liposomes are used to deliver t an NNMT antagonist, or nucleic acids encoding an NNMT antagonist, to a subject. Liposomes may increase the blood half-life of the NNMT antagonist.

Liposomes suitable for use in the invention can be formed from standard vesicle-forming lipids, which generally include neutral or negatively charged phospholipids and a sterol such as cholesterol. The selection of lipids is generally guided by consideration of factors such as the desired liposome size and half-life of the liposomes in the blood stream. A variety of methods are known for preparing liposomes, for example as described in Szoka et al. (1980), *Ann. Rev. Biophys. Bioeng.* 9:467; and U.S. Pat. Nos. 4,235,871, 4,501,728, 4,837,028, and 5,019,369, the entire disclosures of which are herein incorporated by reference.

In some embodiments, NNMT antagonists, or nucleic acids encoding them, are encapsulated in liposomes prior to administration to the subject. The liposomes encapsulating the NNMT antagonists, or nucleic acids encoding them, can comprise a ligand molecule that targets the liposome to a target cell, such as, for example, an adipocyte or a hepatocyte. Preferably, ligands that bind to receptors prevalent in target cells, such as monoclonal antibodies that bind to cell surface markers, are employed.

The liposomes encapsulating the NNMT antagonists, or nucleic acids encoding them, can also be modified so as to avoid clearance by the mononuclear macrophage system ("MMS") and reticuloendothelial system ("RES"). Such modified liposomes have opsonization-inhibition moieties on the surface or incorporated into the liposome structure. In a particularly preferred embodiment, a liposome of the invention can comprise both opsonization-inhibition moieties and a ligand.

Opsonization-inhibiting moieties for use in preparing the liposomes of the invention are typically large hydrophilic polymers that are bound to the liposome membrane. As used herein, an opsonization inhibiting moiety is "bound" to a liposome membrane when it is chemically or physically attached to the membrane, e.g., by the intercalation of a lipid-soluble anchor into the membrane itself, or by binding directly to active groups of membrane lipids. These opsonization-inhibiting hydrophilic polymers form a protective surface layer which significantly decreases the uptake of the liposomes by the MMS and RES; e.g., as described in U.S. Pat. No. 4,920,016, the entire disclosure of which is herein incorporated by reference.

Opsonization inhibiting moieties suitable for modifying liposomes are preferably water-soluble polymers with a number-average molecular weight from about 500 to about 40,000 daltons, and more preferably from about 2,000 to about 20,000 daltons. Such polymers include polyethylene glycol (PEG) or polypropylene glycol (PPG) derivatives; e.g., methoxy PEG or PPG, and PEG or PPG stearate; synthetic polymers such as polyacrylamide or poly N-vinyl pyrrolidone; linear, branched, or dendrimeric polyamidoamines; polyacrylic acids; polyalcohols, e.g., polyvinylalcohol and polyxylitol to which carboxylic or amino groups are chemically linked, as well as gangliosides, such as ganglioside $GM_1$. Copolymers of PEG, methoxy PEG, or methoxy PPG, or derivatives thereof, are also suitable. In addition, the opsonization inhibiting polymer can be a block copolymer of PEG and either a polyamino acid, polysaccharide, polyamidoamine, polyethyleneamine, or polynucleotide. The opsonization inhibiting polymers can also be natural polysaccharides containing amino acids or carboxylic acids, e.g., galacturonic acid, glucuronic acid, mannuronic acid, hyaluronic acid, pectic acid, neuraminic acid, alginic acid, carrageenan; aminated polysaccharides or oligosaccharides (linear or branched); or carboxylated polysaccharides or oligosaccharides, e.g., reacted with derivatives of carbonic acids with resultant linking of carboxylic groups. Preferably, the opsonization-inhibiting moiety is a PEG, PPG, or derivatives thereof. Liposomes modified with PEG or PEG-derivatives are sometimes called "PEGylated liposomes."

The opsonization inhibiting moiety can be bound to the liposome membrane by any one of numerous well-known techniques. For example, an N-hydroxysuccinimide ester of PEG can be bound to a phosphatidyl-ethanolamine lipid-soluble anchor, and then bound to a membrane. Similarly, a dextran polymer can be derivatized with a stearylamine lipid-soluble anchor via reductive amination using $Na(CN)BH_3$ and a solvent mixture such as tetrahydrofuran and water in a 30:12 ratio at 60° C.

Liposomes modified with opsonization-inhibition moieties remain in the circulation much longer than unmodified liposomes. For this reason, such liposomes are sometimes called "stealth" liposomes. Stealth liposomes are known to accumulate in tissues fed by porous or "leaky" microvasculature. Thus, tissue characterized by such microvasculature defects, for example solid tumors, will efficiently accumulate these liposomes; see Gabizon, et al. (1988), *Proc. Natl. Acad. Sci., USA,* 18: 6949-53. In addition, the reduced uptake by the RES lowers the toxicity of stealth liposomes by preventing significant accumulation of the liposomes in the liver and spleen. Thus, liposomes that are modified with opsonization-inhibition moieties are particularly suited to deliver the NNMT antagonists, or nucleic acids encoding them, to target cells.

A description of example embodiments of the invention follows.

Exemplification

Materials and Methods

Materials

All chemicals and reagents were from Sigma Chemical Corp., St. Louis, Mo., except where stated otherwise.

Mice

For all experiments, male C57BL/6 mice from Jackson Laboratories or Charles River Laboratories were used. Mice were fed standard chow providing 17% calories from fat (LabDiet Formulab 5008), or, starting at 6-7 weeks of age, a high-fat diet (HFD) providing 55% calories from fat (Harlan Teklad, TD93075; 4.8 kcal/g). Starting two weeks after the initiation of HFD feeding, NNMT ASO or control ASO were injected at a dose of 37.5 mpk i.p. twice per week. Mice were killed approximately 48 hours after the injection of the last dose.

Experimental protocols were approved by the Institutional Animal Care and Use Committee at Beth Israel Deaconess Medical Center (BIDMC).

Selection of Mouse NNMT ASO

Rapid-throughput screens were performed in primary rat hepatocytes to identify mouse NNMT antisense oligonucleotides. In brief, 80 ASOs were designed to the NNMT mRNA sequence, all of which targeted a binding site within the coding region of the NNMT mRNA. The reduction of target gene expression was analyzed with real-time quantitative RT-PCR after transfection of the cells with ASOs for 24 h. Based on target reduction, 8 ASOs were selected and further characterized in a dose-response screen. The most potent ASOs from the screen were chosen, and their in vivo activity was confirmed in lean C57BL/6 mice. The most potent ASO was chosen as the NNMT ASO for subsequent studies. All of the ASOs screened have a uniform phosphorothioate backbone and a 20-base chimeric design with a 2'-O-(methoxy)-ethyl (2'-MOE) modification on the first 5 and the last 5 bases. This modification enhances their binding affinity to complementary sequences and their resistance to the action of nucleases. A control ASO (ISIS 425851), which has the same chemical composition as the NNMT ASO, but no complementarity to any known gene sequence, was used for the control group.

Metabolic Studies

Body composition was analyzed with a EchoMRI 3-in-1 instrument (Echo Medi-cal Systems, Houston, Tex.).

Oxygen consumption, carbon dioxide production, physical activity, and heat production were measured in a Continuous Laboratory Animal Monitoring System (Columbus Instruments, Columbus, Ohio, USA) by the Mouse Metabolism Core Facility at Beth Israel Deaconess Medical Center. For the purpose of resting energy expenditure calculations, resting was defined as less than 100 laser beam breaks per hour.

Food Intake and Fecal Lipid Excretion

Food intake was measured by weighing wire tops with food repeatedly over time, and subtracting any food that was found in the bedding.

To analyze fecal lipid excretion, several days' worth of feces was manually separated from the bedding. Aliquods of 1000 mg were powderized with pestle and mortar, suspended in 5 ml 0.9% saline in 15-ml tubes, and vortexed vigorously. Then, 5 ml chloroform:methanol (2:1) were added, and the suspension was vortexed again and centrifuged at 1000 g for 10 min at room temperature. The organic phase at the bottom was aspirated by puncturing the tubes with a 22 G needle. For each sample, a glass tube was weighed with maximum precision, and the entire organic phase was transferred to a glass tube. The tubes were air-dried under a fume hood for several days and weighed again to obtain the lipid mass in the collected feces.

Body Temperature

Body temperature was measured intrarectally using a Thermalert TH-5 thermo-meter (Physitemp, Clifton, N.J., USA).

RNA Extraction and Quantitative PCR

For RNA extraction, tissues were homogenized in Tri reagent (Molecular Re-search Center, Cincinnati, Ohio, USA) using a TissueLyzer II bead homogenizer (Qiagen, Valencia, Calif., USA) and processed according to the manufacturer's instructions. Reverse transcription was performed using the Advantage RT-for-PCR kit from Clontech Laboratories, Inc. (Mountain View, Calif., USA), and cDNA was quantified using Taqman probes and primers in a 9700 HT instrument (Applied Biosytems, Foster City, Calif., USA). For quantification, standard curves were generated for each gene using pooled cDNA samples.

Western Blotting and Immunoprecipitation

Snap-frozen tissues were homogenized in lysis buffer (20 mM Tris-HCl, 5 mM EDTA, 10 mM Na4P2O7, 100 mM NaF, 1% Igepal CA-630, 10 μg/ml aprotinin, 10 μg/ml leupeptin, 1 mM PMSF, 2 mM Na3VO4) using a TissueLyzer II bead homoge-nizer (Qiagen) at 30 Hz for 1 min. Homogenates were centrifuged at 16,100 g for 15 minutes at 2° C. Protein concentration in the supernatant was quantified using the bicinchoninic acid assay and adjusted with lysis buffer. Samples were submitted to SDS-PAGE (Criterion gels, Bio-Rad, Hercules, Calif.) and transferred to nitrocellulose membranes (Schleicher & Schuell) with 0.45 μm pores (0.2 μm for NNMT Western blotting). After blocking with 5% milk/TBST for 1 hour at room temperature, membranes were probed with specific antibodies over night at 4° C.

The following antibodies were used: Rabbit anti-PEPCK from Cayman Chemical, Ann Arbor, Mich., USA; goat anti-UCP1 (M-17), goat anti-troponin I—SS (C-19), rabbit anti-PGC1α (H-300), and rabbit anti-β-actin (I-19) from Santa Cruz Biotechnology, Santa Cruz, Calif., USA; rabbit anti-pThr172-AMPK, rabbit anti-ACC, rabbit anti-acetylated lysine from Cell Signaling Technology, Beverly, Mass., USA; rabbit anti-α1-AMPK, rabbit anti-phospho-acetyl CoA carboxylase (pACC, Ser79), rabbit anti-p85 from Upstate/Millipore, Billerica, Mass., USA. The rabbit anti-NNMT antibody was a kind gift of Dr. Richard Weinshilboum (Rochester, Minn., USA) (2).

For PGC1α immunoprecipitation, snap-frozen tissue was powderized on liquid nitrogen, suspended in hypotonic lysis buffer, and processed with a hand-held homogenizer. Homogenates were centrifuged for 3 min at 4000/min. The pellets were resuspended in RIPA buffer, vortexed, and centrifuged for 15 min at 16,100 g. Protein concentration in the supernatant was determined as described above. For immunoprecipitation, 3 mg of nuclear protein and 2 μg of anti-PGC1α antibody (H-300; Santa Cruz Biotechnology, Santa Cruz, Calif., USA) antibody were rotated over night at 4° C.

Chemiluminescence (Western Lightning ECL Plus, Pierce/Thermo Fisher Scientific, Rockfort, Ill., USA) was detected using film (Fuji Medical RX-U) and camera (GeneGnome, Synoptics, Inc., Frederick, Md., USA). Bands were quantified using the software ImageQuant TL (GE Healthcare, Piscataway, N.J., USA).

Ornithine Decarboxylase Activity

To determine ornithine decarboxylase (ODC) activity, snap-frozen tissues were homogenized on ice with a TissueTearor hand-held homogenizer in activity assay buffer (50 mM Tris-HCl, pH 7.5, 2.5 mM dithiotreitol, 5 mM EDTA, 0.5 mM PMSF) and centrifuged for 10 min at 16,100 g. To ensure that the activity was in the linear range for the assay, protein concentration in the supernatants was determined with the RC/DC kit from Bio-Rad and adjusted to 1 g/l in 14-ml tubes (Falcon 352059). For determination of specific ODC activity, two sets of samples were prepared; one of these was supplemented with 1 mM difluoromethylornithine (DFMO). The reaction was started by adding 100 μM pyridoxalphosphate and 500 nCi [1-14C]-L-ornithine (Moravek Bio-chemicals, Brea, Calif., USA; specific activity 52 mCi/mmol; final concentration of ornithine 18.2 μM). The tubes were sealed with rubber stopper tops from which center wells with filter paper were suspended. After 60 minutes at 37° C. in a shaking water bath, the reaction was stopped by careful injection of 400 μl of 2 N sulfuric acid through the rubber tops into the tubes. The filter paper was soaked by injecting 300 μl of 1 M benzethonium hydrochloride, and the released carbon dioxide was trapped during 30 minutes at 37° C. in the shaking water bath. The stopper tops and center wells were transferred to liquid scintillation cocktail (Fisher Scinti-Safe 50% Plus), and radioactivity was counted in a Beckman LS counter. ODC activity in each sample was calculated as the difference of counts without DFMO and counts with DFMO.

Metabolites

NAD+ concentrations in tissues were measured using a colorimetric kit (Bio-Assay Systems, Hayward, Calif., USA) according to the manufacturer's instructions. Nicotinamide and N-methylnicotinamide were measured by HPLC.

Liver Glycogen Content

Pieces of snap-frozen liver were weighed (~10-15 mg), placed in 300 μl 0.5 N KOH, incubated for 30 min at 95° C., and vortexed. 25 μl 6% sodium sulfate and 750 μl ethanol were added to each sample. Following incubation at −80° C. for 20 min, samples were centrifuged at 16,100 g for 20 min at 4° C. The pellets were suspended in 1 ml of 70% ethanol, incubated for 10 min at −20° C., and centrifuged at 16,100 g for 5 min at 4° C. The supernatant was entirely removed, and 120 μl of amyloglucosidase (2 mg/ml in sodium acetate, pH 4.9) was added. The samples were vortexed until the pellets were resuspended, then incubated at 37° C. for 60 min, and centrifuged at 16,100 g for 5 min. A 5-μl aliquot from each sample was transferred to a 96-well plate. 200 μA of glucose oxidase reagent (Thermo Fisher Scientific, Waltham, Mass., USA) was added, and the plate was incubated at 37° C. for 10 min. Absorption was read at 500 nm with reference wavelength 600 nm. A glycogen standard curve (type III, rabbit liver) was included in each assay.

Histology and Determination of Cell Size

Tissues were fixed in 10% buffered formalin and submitted to the Histology Core at BIDMC for paraffin embedding and H&E staining.

To measure adipocyte cell sizes, several fields of vision of H&E-stained adipose tissue were digitally photographed under a microscope. Images were analyzed using the software ImageJ (National Institutes of Health, Bethesda, Md., USA) using a published technique (19). Briefly, images were converted to 16-bit grayscale and inverted; a threshold was applied to identify cell boundaries, and the cells were analyzed with the "Analyze Particles" command.

Cell Culture

3T3-L1 were grown in Dulbecco's Modified Eagle's Medium (Gib-co/Invitrogen, Carlsbad, Calif., USA) with 4.5 g/l glucose and 10% fetal bovine serum. Differentiation was induced in two-day-postconfluent cells by supplementing the media with 1 μM insulin, 100 nM dexamethasone, and 500 μM isobutylmethylxanthine for 48 hours, followed by media supplemented with 1 μM insulin for another 48 hours, then normal media until differentiation day 10.

Transduction of 3T3-L1 adipocytes with NNMT adenovirus was performed according to the protocol by Orlicky & Schaack (20). Briefly, adenovirus was incubated at the indicated concentrations in normal media in the presence of 1 μg/ml poly-L-lysine for 1.5 hours. The suspension was then added to cells washed with PBS and incubated for 1.5 hours, after which normal media was added to the wells.

Oxygen Consumption

Oxygen consumption was measured with a Rank Brothers oxygen electrode (Rank Brothers Ltd., Cambridge, UK). Cultured cells were trypsinized, counted in a hemocytometer, spun down, and resuspended in respiration buffer (PBS, 2% BSA, 4.5 g/l glucose, 120 mg/l sodium pyruvate) to 1E6/ml. Partial oxygen pressure was recorded using a Rank Brothers digital model 10 and a PowerLab 4/30 data acquisition system (ADInstruments, Colorado Springs, Colo.).

Glucose Uptake in 3T3-L1

Fully differentiated 3T3-L1 adipocytes (day 10) in 48-well plates were serum-starved for 1 hour before incubation with Krebs-Ringer-HEPES (KRH) buffer with or without 10 nM insulin for 30 minutes, followed by addition of 1 mM, 100 nCi [3H]-2-deoxyglucose for 10 minutes. Uptake was stopped by lysing the cells with 0.1% sodium dodecyl sulfate (SDS). Lysates were transferred to liquid scintillation cocktail (Fisher Scinti-Safe 50% Plus) and counted in a Beckman LS counter.

Lipolysis

Fully differentiated 3T3-L1 adipocytes (day 10) in 48-well plates were washed, and 100 μl of KRH buffer with 3% BSA and 4 g/l D-glucose with or without 100 nM isoproterenol was added to each well. After 1 hour at 37° C./5% CO2 a 50 μl aliquot from each well was transferred to a 96-well plate; 50 μl of lipolysis assay buffer (Cayman Chemical) were added, and the plate was incubated at room temperature, protected from light, for 30 min. Absorption was measured at 540 nm. A standard curve was included on each plate to allow calculation of the glycerol concentration in the supernatants.

Statistical Analysis

To compare two groups, Student's t test was used. To compare many groups, analyses of variance were performed, followed by Bonferroni-Holm post tests. Statistical significance is assumed for $p<0.05$. For the sake of clarity, a single asterisk is used to denote any level of significance (including $p<0.01$ and $p<0.001$) in the figures.

Results

Figure 2:
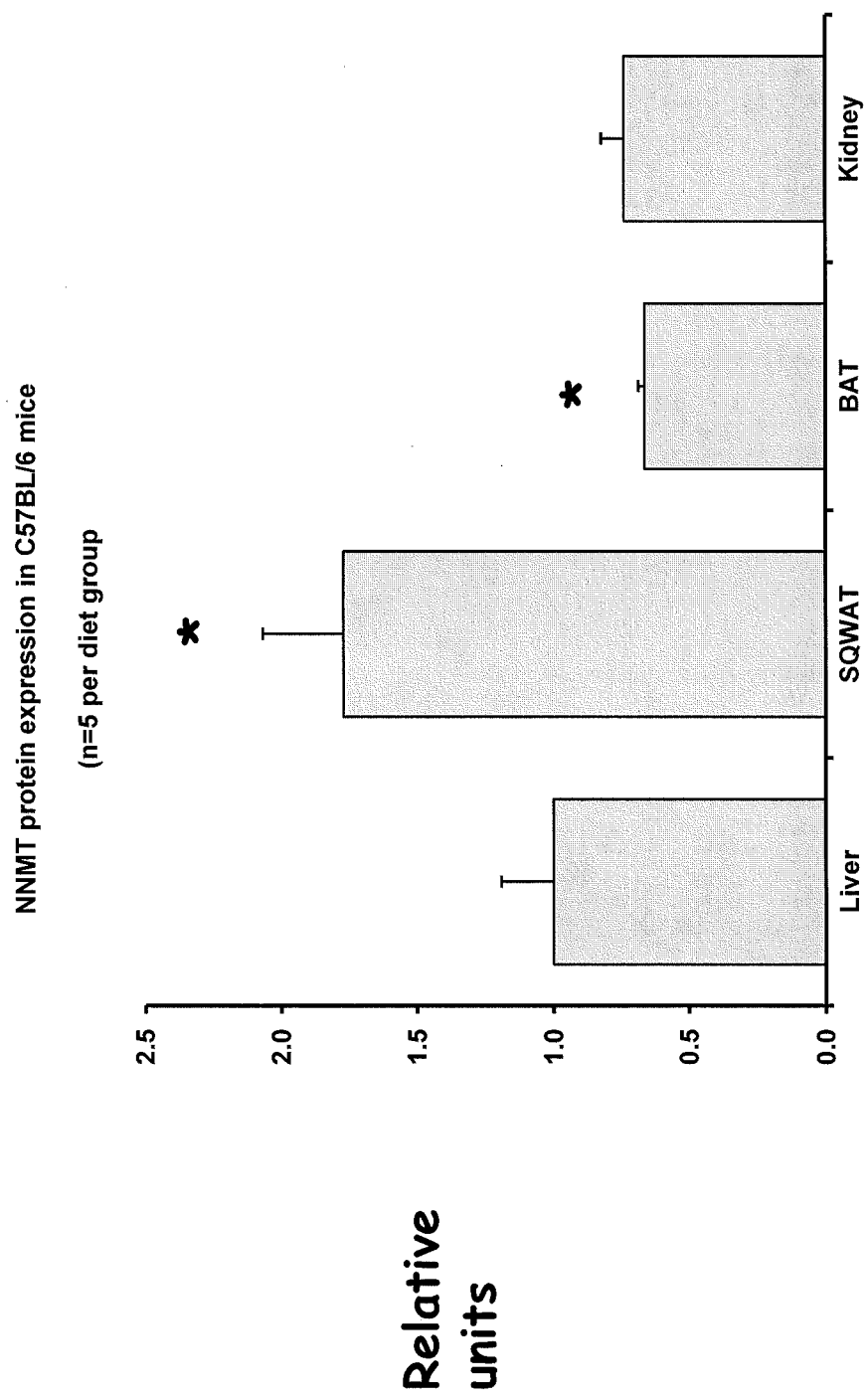
FIG. 2 is a graph depicting NNMT expression in various tissues of C57BL/6 mice.

NNMT protein was previously known to be highly expressed in liver, kidney, and few other tissues (Yan 1997); expression data for adipose tissue had not been previously reported. Interestingly, in male C57BL/6 mice, NNMT protein expression in white, but not brown, adipose tissue is about 1.8-fold higher than in liver (FIG. 2), indicating that adipose tissue NNMT may have an important physiological role.

Figures 3A, 3B:
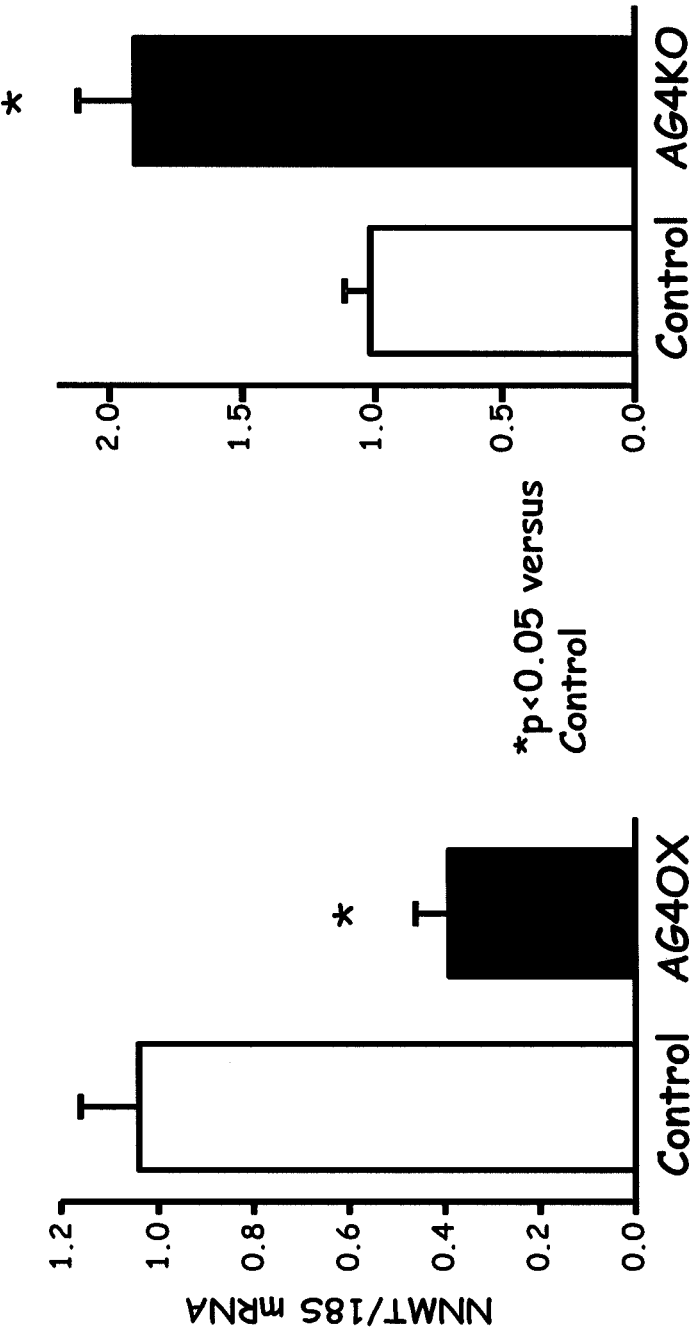
FIGS. 3A and B are graphs depicting inverse regulation of NNMT expression in white adipose tissue of mice with altered Glut4 expression in adipose tissue.
FIG. 3B is a graph depicting increased NNMT mRNA expression in white adipose tissue of insulin resistant adipose-specific Glut4 knockout mice (AG4KO).

NNMT mRNA levels were reduced by 62% in adipose tissue of AG4OX mice (FIG. 3A) and increased 2-fold in adipose tissue of AG4KO mice (FIG. 3B). NNMT protein levels are increased in liver and fat of common mouse models of obesity and insulin resistance, compared with lean controls. Specifically, NNMT protein is increased in WAT of high fat diet (HFD)-fed and obese ob/ob mice (FIGS. 4A, B), as well as in liver of obese ob/ob and obese and diabetic db/db mice (FIGS. 4C, D). These results suggest that NNMT expression is upregulated in adipose tissue and liver in obesity and insulin resistance.

NNMT overexpression may a have causative role in the pathogenesis of diabetes and obesity; suppression of NNMT could reverse these conditions. To test this hypothesis, antisense oligonucleotides (ASO) were used to knock down NNMT in diet-induced obese (DIO) C57BL/6 mice over a course of several weeks.

ASOs have been shown to regulate gene expression specifically in liver and fat, but not in muscle (Samuel, Diabetes 2006; Samuel, JCI 2007; Choi 2007). Treating DIO mice with NNMT ASO at a dose of 37.5 mg/kg body weight twice per week reduced NNMT protein expression by 62.6% in liver (FIG. 5A) and by 75.2% in white adipose tissue (FIG. 5B). NNMT expression was not altered by NNMT ASO treatment in brown adipose tissue (FIG. 5C) and in kidney (FIG. 5D). NNMT could not be detected in skeletal muscle. Serum liver transaminases and creatinine were normal in mice treated with NNMT and control ASOs indicating there was no hepatic and renal toxicity associated with ASO treatment (not shown).

Figures 6A, 6B, 6C:
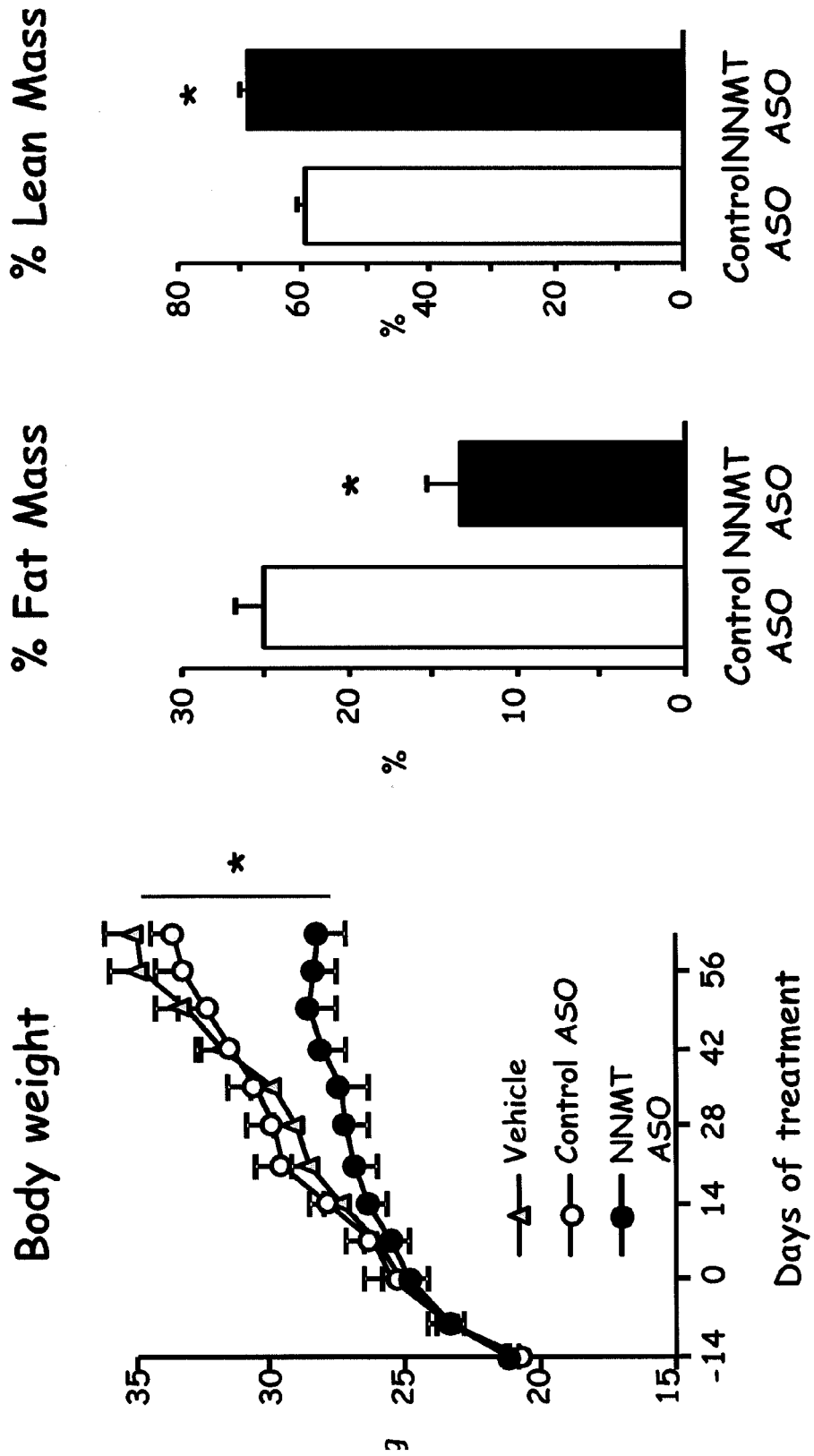
FIGS. 6A-C are graphs showing that knockdown of NNMT expression using antisense oligonucleotides (ASO) protects against diet-induced obesity.
Figure 7C:
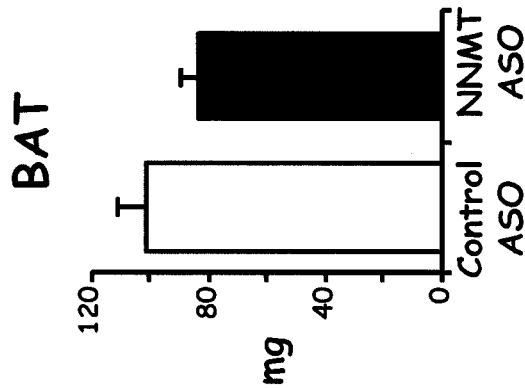
FIG. 7C is a graph showing that NNMT knockdown using NNMT ASO did not significantly reduce brown adipose tissue (BAT) mass in mice on a high fat diet relative to Control ASO.
Figure 7B:
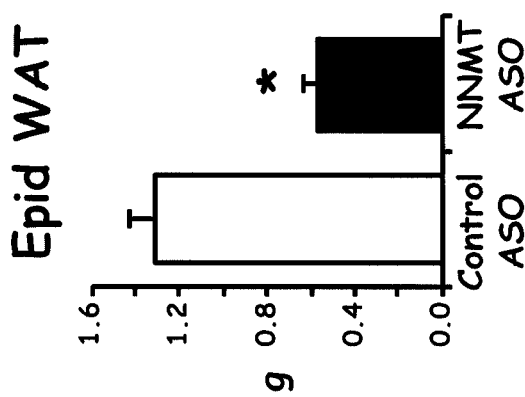
FIG. 7B is a graph showing that NNMT knockdown using NNMT ASO reduces epididymal white adipose tissue (Epid WAT) mass in mice on a high fat diet relative to Control ASO.
Figure 7A:
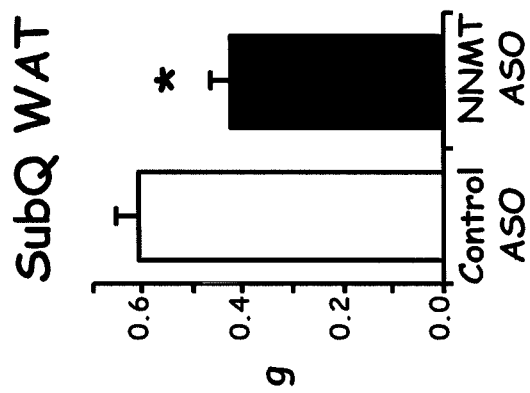
FIG. 7A is a graph showing that NNMT knockdown using NNMT ASO reduces subcutaneous white adipose tissue (SubQ WAT) mass in mice on a high fat diet relative to Control ASO.
Figure 7E:
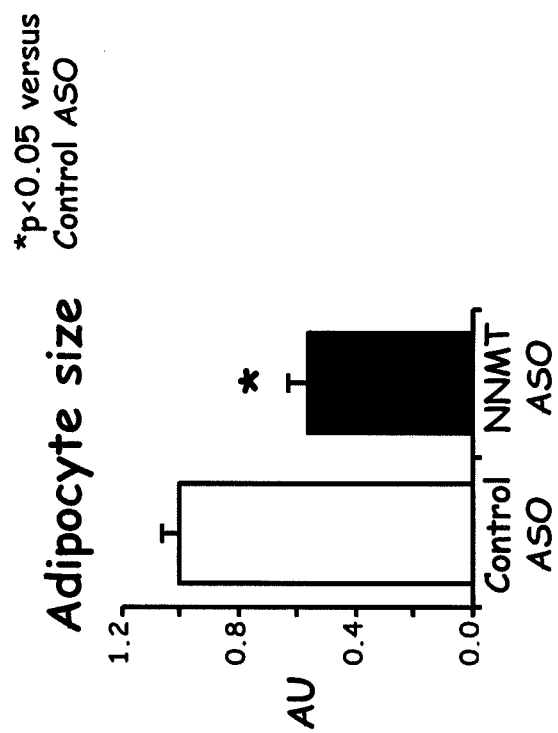
FIG. 7E is a graph depicting that NNMT knockdown using NNMT ASO reduces adipocyte size in epididymal white adipose tissue in mice on a high fat diet relative to control.
Figure 7D:
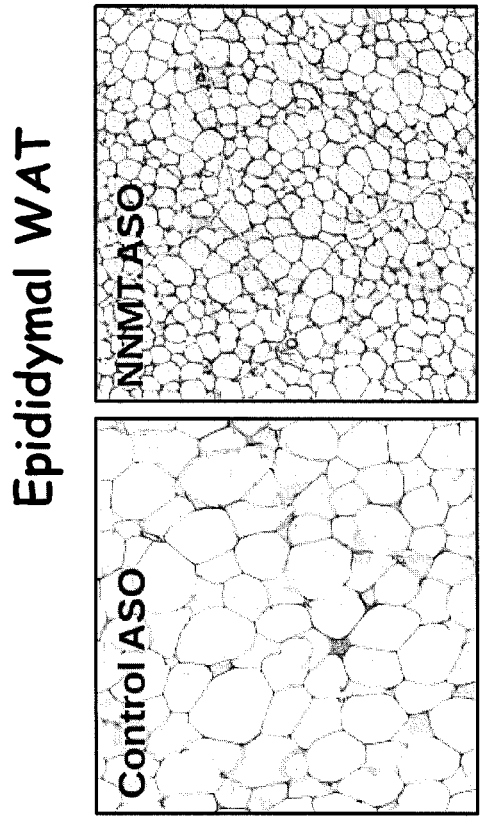
FIG. 7D are epididymal white adipose tissue sections showing that NNMT knockdown using NNMT ASO reduces adipocyte size in mice on a high fat diet relative to control.

NNMT knockdown in fat and liver protected mice from diet-induced obesity (FIG. 6A). After 8 weeks of treatment, adiposity was reduced by 46.8% (FIG. 6B), and lean body mass expressed as percent of whole body mass was increased by 14.9% (FIG. 6C) in NNMT-knockdown mice compared with control ASO-treated mice. Accordingly, subcutaneous (FIG. 7A) and epididymal (FIG. 7B) white fat pad masses were significantly lower in NNMT-knockdown mice than in control mice. Brown adipose tissue weight was not significantly altered (FIG. 7C). The decreased white fat pad weight was largely due to a 44.2% reduction in cell size of adipocytes (FIG. 7D, E).

Figures 9A, 9B, 9C:
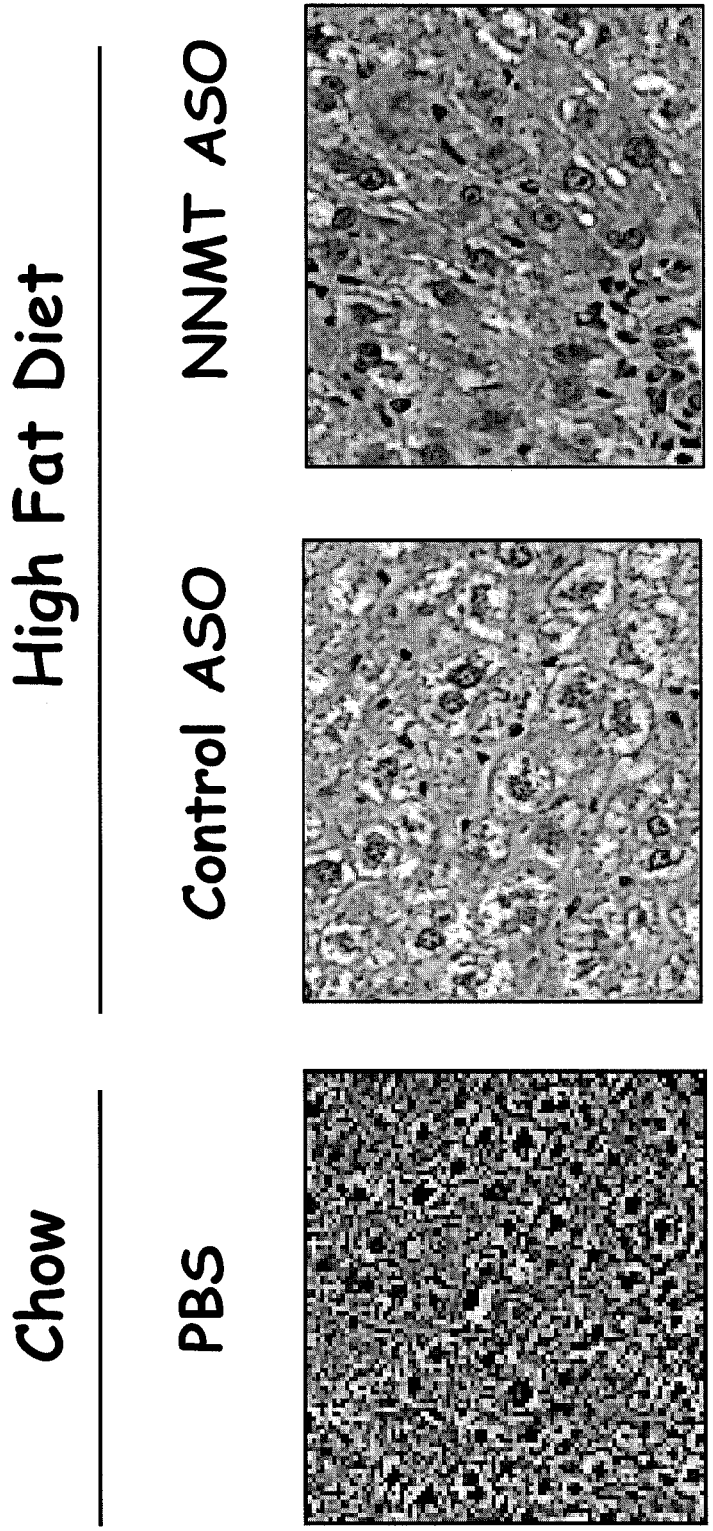
FIGS. 9A-C are hematoxylin and eosin (H&E) stained liver tissue sections of mice fed either chow (FIG. 9A) or a high fat diet (FIGS. 9B,C). Lipid deposits appear white. Treatment with NNMT ASO reduced the number of lipid deposits in liver tissue (FIG. 9B) relative to control (FIG. 9C) in mice that were fed high fat diets.

Random-fed glycemia tended to be lower (FIG. 8A), and corresponding serum insulin levels were significantly reduced by 48% (FIG. 8B). NNMT-knockdown mice exhibited improved glucose tolerance (FIG. 8C). NNMT ASO treatment reduced diet-induced hepatic steatosis (FIG. 9B).

Figures 10A, 10B, 10C:
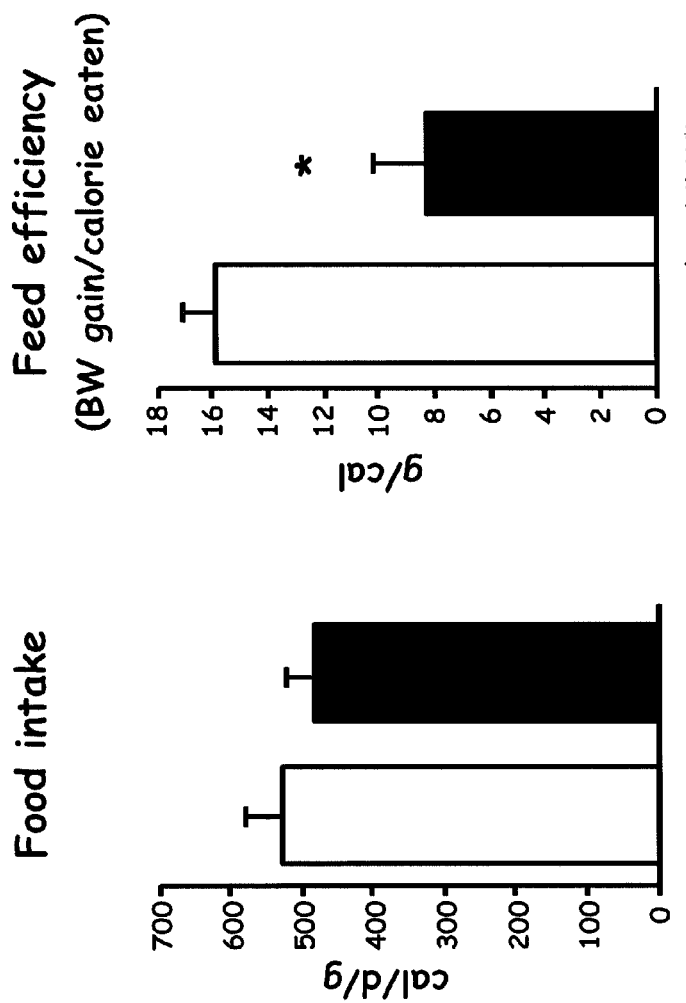
FIGS. 10A-C are graphs showing that NNMT knockdown using antisense oligonucleotide (ASO) decreases feed efficiency.

Mice treated with NNMT ASO consumed the same amount of calories as mice treated with control ASO (FIG. 10A). Feed efficiency, defined as the change in body weight for each unit of food eaten, was significantly reduced in NNMT-knockdown mice (FIG. 10B). While mice treated with control ASO gained about 7 mg of fat for each kcal of food intake, NNMT-ASO-treated mice lost body fat on average (FIG. 10C). These results suggest that increased energy expenditure rather than decreased food intake is responsible for the leanness in NNMT-knockdown mice.

Figures 11A, 11B, 11C:
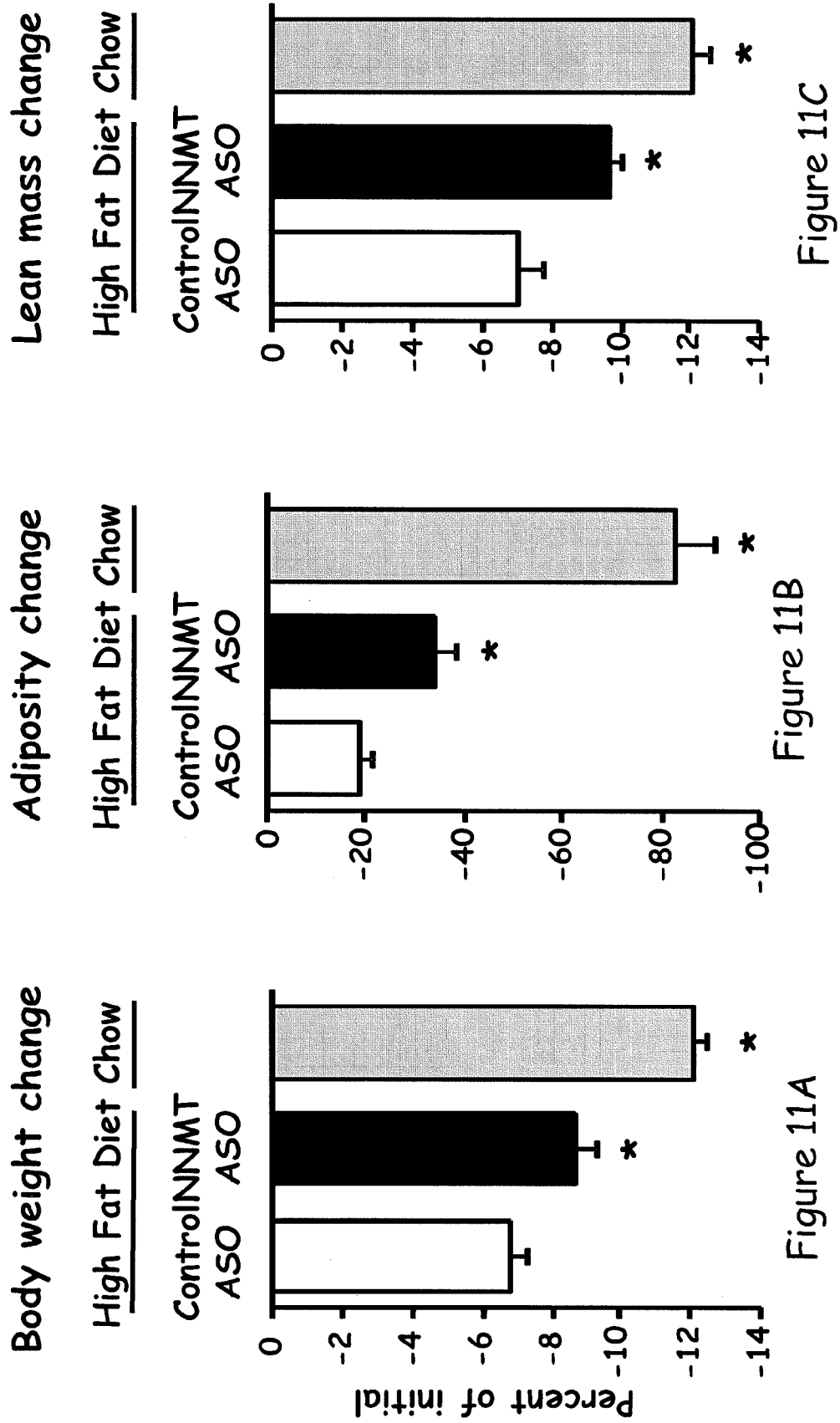
FIGS. 11A-C are graphs showing that NNMT knockdown using antisense oligonucleotide (ASO) results in greater weight loss during fasting.

When subjected to a 16-hour fast, NNMT-knockdown mice lost significantly more body weight (FIG. 11A), body fat (FIG. 11B), and even lean mass (FIG. 11C) than control ASO-treated mice, resembling the response of chow-fed lean mice. These data suggest that increased energy expenditure, rather than changes in food intake or malabsorption is the primary cause for the leanness in NNMT ASO-treated mice.

Figures 12A, 12B, 12C:
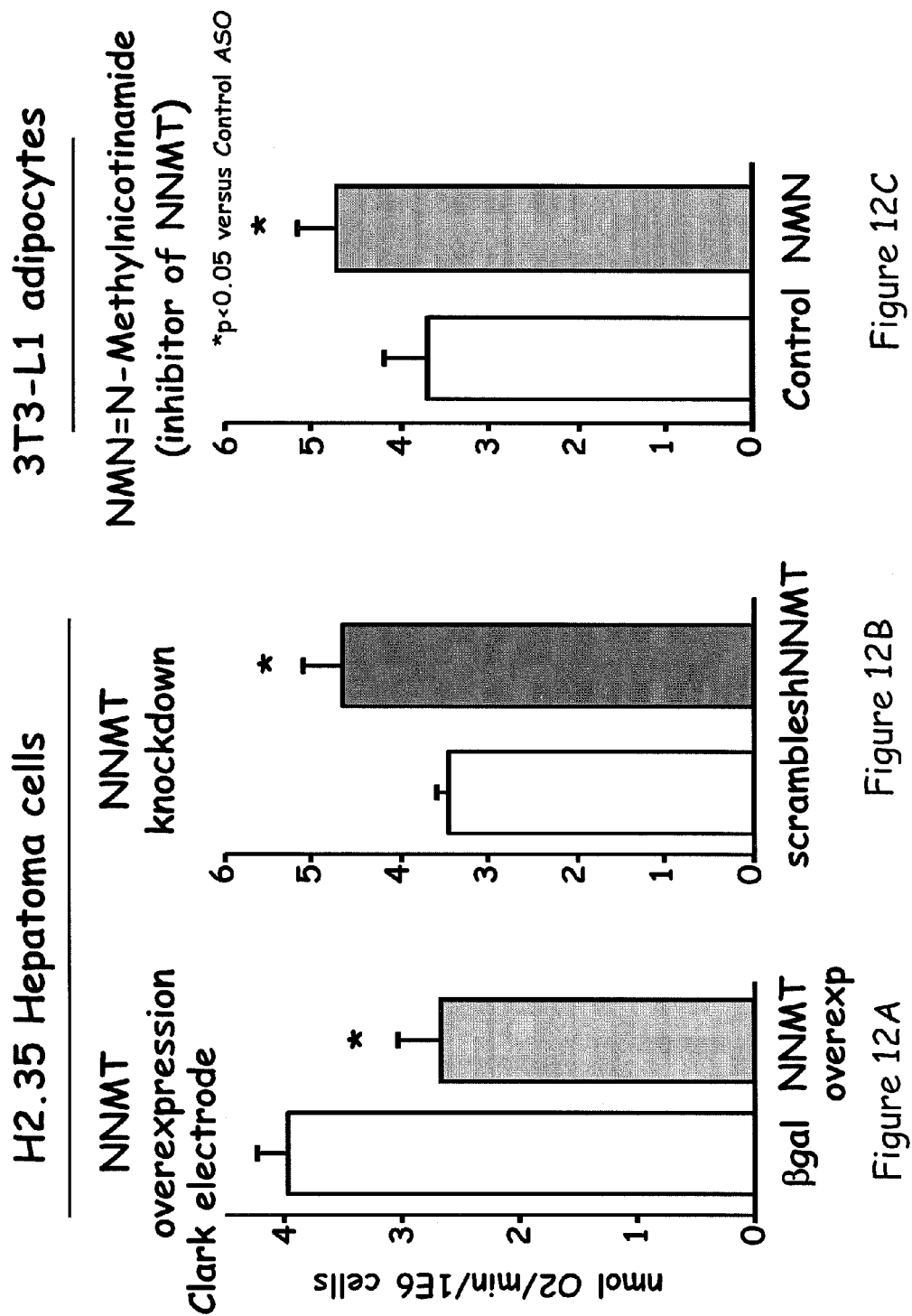
FIGS. 12A-C are graphs showing that altered NNMT activity affects $O_2$ consumption in cultured H2.35 hepatoma cells and 3T3-L1 adipocytes.
Figures 13A, 13B:
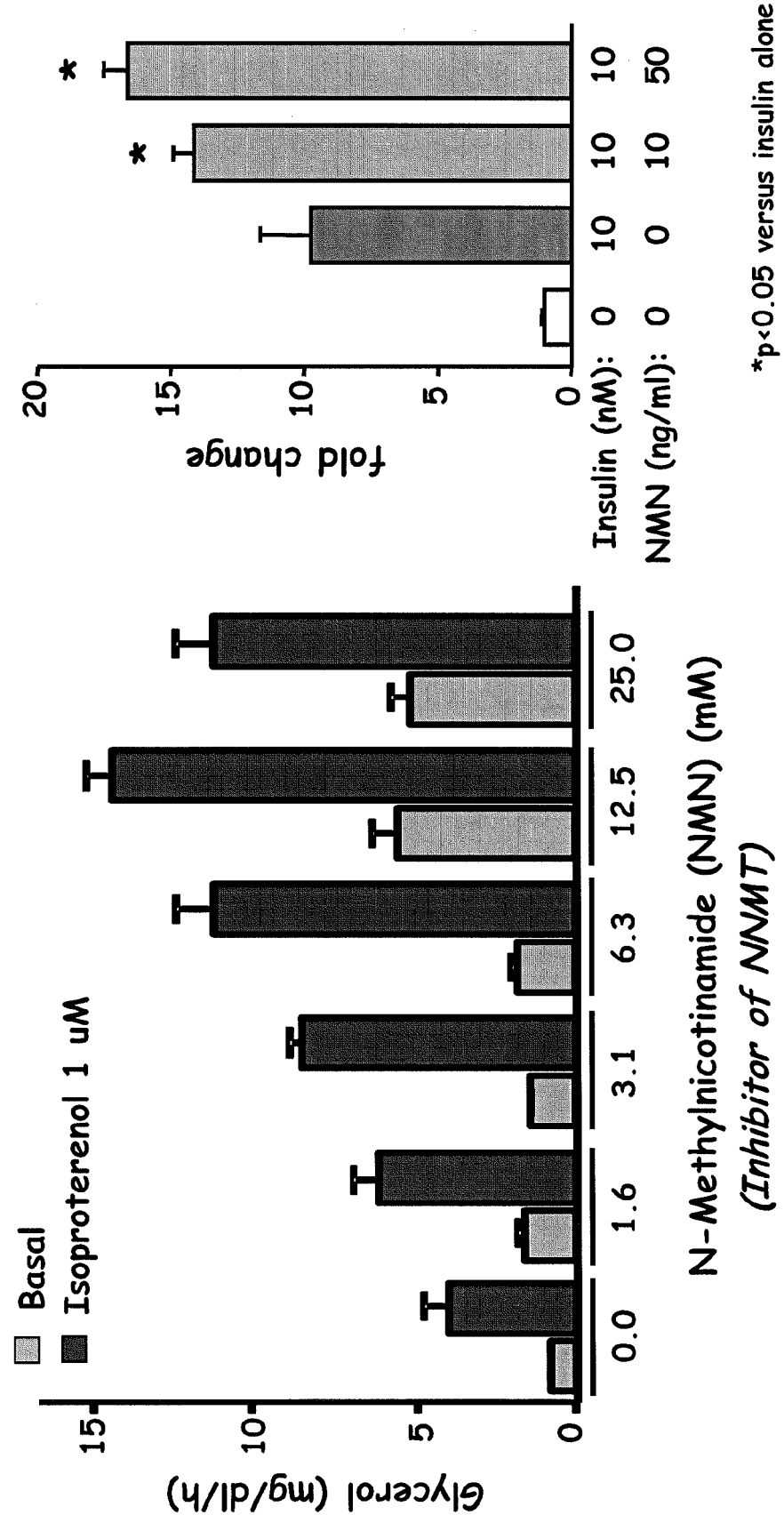
FIG. 13A is a graph depicting the biological effect of inhibition of NNMT on lipolysis in 3T3-L1 adipocytes following treatment with NMN, an inhibitor of NNMT.
FIG. 13B is a graph depicting the biological effect of inhibition of NNMT on glucose uptake in 3T3-L1 adipocytes following treatment with NMN, an inhibitor of NNMT.

To establish whether NNMT regulates energy expenditure at a cell-autonomous level, oxygen consumption of cultured cells was measured using a Clark electrode. Adenovirally-mediated NNMT overexpression in H2.35 mouse hepatoma cells decreased oxygen consumption (FIG. 12A), while short hairpin RNA-induced silencing of NNMT caused increased oxygen consumption (FIG. 12B). Treating differentiated 3T3-L1 adipocytes with the pharmacological NNMT inhibitor, N-methylnicotinamide, also caused increased oxygen consumption (FIG. 12C). Furthermore, pharmacological inhibition of NNMT increased lipolysis in cultured 3T3-L1 adipocytes, as measured by the amount of glycerol released into the culture supernatant (FIG. 13A), and stimulated insulin-dependent glucose uptake into 3T3-L1 adipocytes (FIG. 13B), indicating increased metabolic turnover in these cells.

Ornithine decarboxylase (ODC) and spermidine-spermine acetyltransferase (SSAT) are the two key enzymes involved in the metabolism of polyamines (Casero and Marton, 2007). It was recently reported that increasing the metabolic flux through the polyamine pathway reduces adiposity, possibly by wasting energy in the form of ATP and acetyl CoA (Jell et al., 2007; Pirinen et al., 2007). Conversely, inhibiting polyamine flux by knocking out SSAT may cause obesity (Jell et al., 2007). SSAT and ODC appear to be linked by a positive feedback loop, as transgenic overexpression of SSAT entails a compensatory increase in ODC activity.

Injection of rodents with nicotinamide, the substrate of NNMT, stimulates ODC activity (Rosenberg et al., 1986; Minaga et al., 1978). Thus it was hypothesized that NNMT knockdown may cause intracellular accumulation of nicotinamide, resulting in heightened SSAT and ODC activity and stimulated energy expenditure.

In mice treated with NNMT ASO and fed a high-fat diet, ODC activity was increased in liver (FIG. 14A) and tended to be increased in WAT (FIG. 14B). NNMT knockdown also stimulated SSAT expression in WAT (FIG. 14C). Adenovirally-mediated NNMT overexpression in 3T3-L1 adipocytes strongly induced ODC activity (FIG. 14D).

Figures 15A, 15B, 15C:
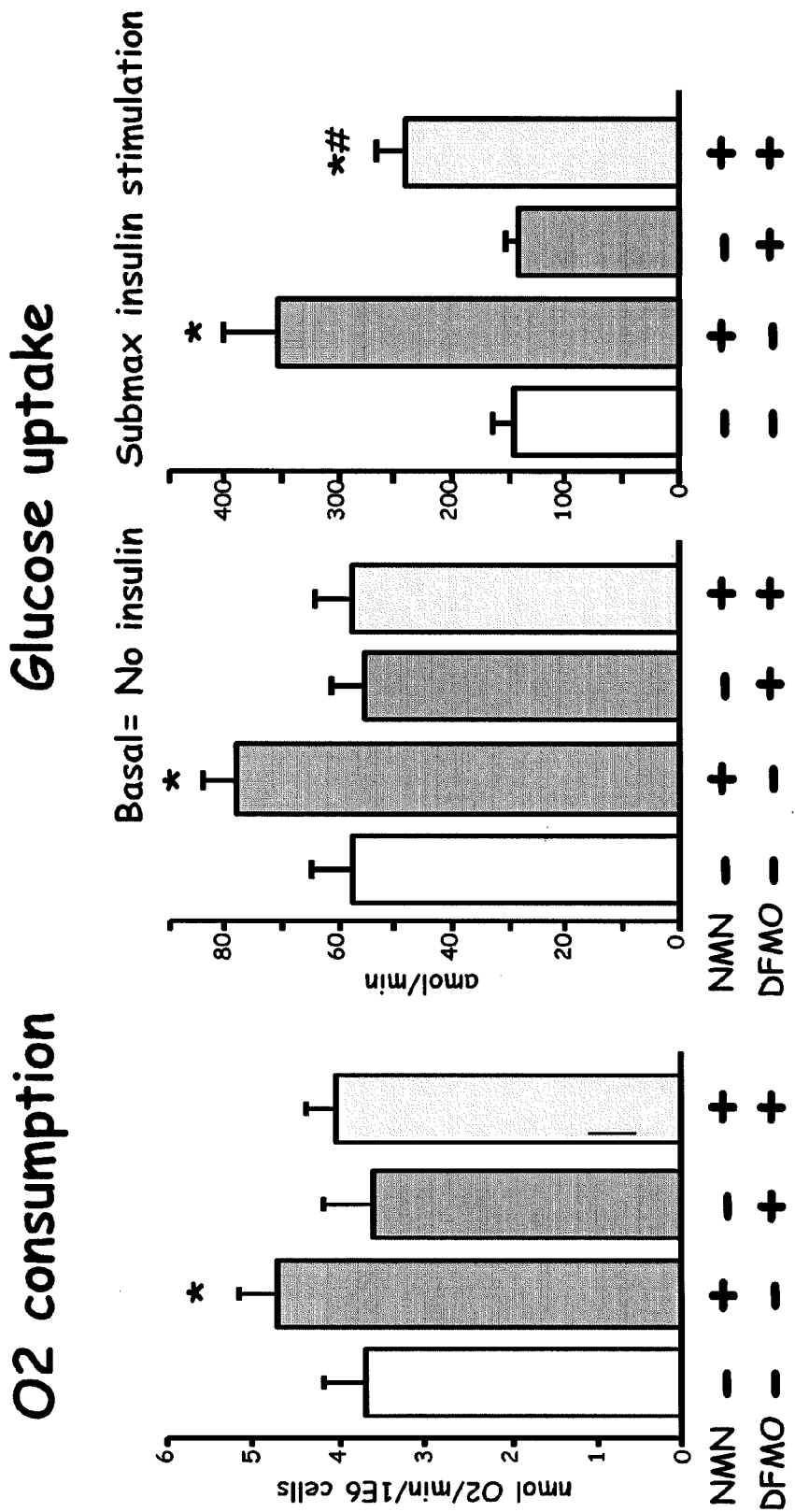
FIGS. 15A-C are graphs showing that the ODC inhibitor, DFMO, blocks the effects of NNMT inhibition in 3T3-L1 adipocytes.

As shown earlier, pharmacological inhibition of NNMT with N-methylnicotinamide stimulated oxygen consumption in cultured hepatoma cells (FIG. 15A). Co-treatment of the cells with the specific ODC inhibitor, difluoromethylornithine (DFMO) abrogated the effect (FIG. 15A), which supports the hypothesis that the regulation of energy expenditure by NNMT involves changes in polyamine metabolism. Moreover, pharmacological inhibition of NNMT stimulated basal (FIG. 15B) and submaximally insulin-induced (FIG. 15C) glucose uptake, and both effects were inhibited by concomitant inhibition of ODC (FIG. 14D).

The teachings of all patents, published applications and references cited herein are incorporated by reference in their entirety.

While this invention has been particularly shown and described with references to example embodiments thereof, it will be understood by those skilled in the art that various changes in form and details may be made therein without departing from the scope of the invention encompassed by the appended claims.

What is claimed is:

1. A method of inhibiting the expression or activity of a nicotinamide N-methyltransferase (NNMT) protein in a cell, comprising providing the cell with an effective amount of at least one NNMT antagonist, wherein the NNMT antagonist is a nucleic acid that inhibits production of NNMT protein, one or more activities of an NNMT protein, or a combination thereof, and wherein the cell is an adipocyte or a hepatocyte.

2. The method of claim 1, wherein the nucleic acid is selected from the group consisting of an antisense oligonucleotide, an siRNA, a microRNA, an aptamer and a ribozyme.

3. The method of claim 2, wherein the nucleic acid is an antisense oligonucleotide.

4. The method of claim 3, wherein the antisense oligonucleotide selectively hybridizes to NNMT mRNA.

5. The method of claim 3, wherein the antisense oligonucleotide comprises RNA.

6. The method of claim 3, wherein the antisense oligonucleotide comprises DNA.

7. The method of claim 3, wherein the antisense oligonucleotide includes at least one chemical modification.

8. The method of claim 7, wherein at least one chemical modification is a phosphorothioate internucleoside linkage, a 2'-O-methoxyethyl sugar modification, a 2'-fluoro sugar modification or a 5-methylcytosine nucleobase.

9. A method of treating or preventing obesity in a subject in need thereof, comprising administering to the subject an effective amount of a nicotinamide N-methyltransferase (NNMT) antagonist, wherein the NNMT antagonist inhibits production of NNMT protein, one or more activities of an NNMT protein, or a combination thereof.

10. The method of claim 9, wherein the NNMT antagonist is a nucleic acid.

11. The method of claim 10, wherein the nucleic acid is selected from the group consisting of an antisense oligonucleotide, an siRNA, a microRNA, an aptamer and a ribozyme.

12. The method of claim 11, wherein the nucleic acid is an antisense oligonucleotide.

13. The method of claim 12, wherein the antisense oligonucleotide selectively hybridizes to NNMT mRNA.

14. The method of claim 12, wherein the antisense oligonucleotide comprises RNA.

15. The method of claim 12, wherein the antisense oligonucleotide comprises DNA.

16. The method of claim 12, wherein the antisense oligonucleotide includes at least one chemical modification.

17. The method of claim 16, wherein at least one chemical modification is a phosphorothioate internucleoside linkage, a 2'-O-methoxyethyl sugar modification, a 2'-fluoro sugar modification or a 5-methylcytosine nucleobase.

18. The method of claim 9, wherein the subject is obese.

19. The method of claim 9, wherein the subject has a metabolic disorder selected from the group consisting of insulin resistance, type 2 diabetes, hyperglycemia and Metabolic Syndrome, or a combination thereof.

20. A method of treating or preventing a metabolic disorder in a subject in need thereof, comprising administering to the subject an effective amount of a nicotinamide N-methyltransferase (NNMT) antagonist, wherein the NNMT antagonist inhibits production of NNMT protein, one or more activities of an NNMT protein, or a combination thereof.

21. The method of claim 20, wherein the metabolic disorder is selected from the group consisting of insulin resistance, type 2 diabetes, hyperglycemia and Metabolic Syndrome, or a combination thereof.

22. The method of claim 20, wherein the NNMT antagonist inhibits production of NNMT protein.

23. The method of claim 20, wherein the NNMT antagonist inhibits an activity of an NNMT protein.

24. The method of claim 20, wherein the NNMT antagonist is a nucleic acid.

25. The method of claim 24, wherein the nucleic acid is selected from the group consisting of an antisense oligonucleotide, an siRNA, a microRNA, an aptamer and a ribozyme.

26. The method of claim 25, wherein the nucleic acid is an antisense oligonucleotide.

27. The method of claim 26, wherein the antisense oligonucleotide selectively hybridizes to NNMT mRNA.

28. The method of claim 26, wherein the antisense oligonucleotide comprises RNA.

29. The method of claim 26, wherein the antisense oligonucleotide comprises DNA.

30. The method of claim 26, wherein the antisense oligonucleotide includes at least one chemical modification.

31. The method of claim 30, wherein at least one chemical modification is a phosphorothioate internucleoside linkage, a 2'-O-methoxyethyl sugar modification, a 2'-fluoro sugar modification or a 5-methylcytosine nucleobase.

32. The method of claim 20, wherein the subject is obese.

33. The method of claim 20, wherein the subject has insulin resistance.

34. The method of claim 20, wherein the subject has type 2 diabetes.

* * * * *

UNITED STATES PATENT AND TRADEMARK OFFICE
CERTIFICATE OF CORRECTION

| | | |
|---|---|---|
| PATENT NO. | : 9,072,766 B2 | Page 1 of 1 |
| APPLICATION NO. | : 13/885284 | |
| DATED | : July 7, 2015 | |
| INVENTOR(S) | : Kahn et al. | |

It is certified that error appears in the above-identified patent and that said Letters Patent is hereby corrected as shown below:

In the specification,

Column 1, Lines 16-19 delete "The invention was supported, in whole or in part, by NIDDK/NIH grant number DK43051 and a grant 09POST2250499 from American Heart Association. The Government has certain rights in the invention."

and insert --This invention was made with government support under grant DK043051 awarded by NIH. The government has certain rights in the invention.--

Signed and Sealed this
Third Day of May, 2016

Michelle K. Lee
*Director of the United States Patent and Trademark Office*

SEQUENCE LISTING

```
<160> NUMBER OF SEQ ID NOS: 2

<210> SEQ ID NO 1
<211> LENGTH: 264
<212> TYPE: PRT
<213> ORGANISM: Homo Sapiens

<400> SEQUENCE: 1

Met Glu Ser Gly Phe Thr Ser Lys Asp Thr Tyr Leu Ser His Phe Asn
 1               5                  10                  15

Pro Arg Asp Tyr Leu Glu Lys Tyr Tyr Lys Phe Gly Ser Arg His Ser
             20                  25                  30

Ala Glu Ser Gln Ile Leu Lys His Leu Leu Lys Asn Leu Phe Lys Ile
         35                  40                  45

Phe Cys Leu Asp Gly Val Lys Gly Asp Leu Leu Ile Asp Ile Gly Ser
     50                  55                  60

Gly Pro Thr Ile Tyr Gln Leu Leu Ser Ala Cys Glu Ser Phe Lys Glu
 65                  70                  75                  80

Ile Val Val Thr Asp Tyr Ser Asp Gln Asn Leu Gln Glu Leu Glu Lys
                 85                  90                  95

Trp Leu Lys Lys Glu Pro Glu Ala Phe Asp Trp Ser Pro Val Val Thr
```

```
            100                 105                 110
Tyr Val Cys Asp Leu Glu Gly Asn Arg Val Lys Gly Pro Glu Lys Glu
        115                 120                 125

Glu Lys Leu Arg Gln Ala Val Lys Gln Val Leu Lys Cys Asp Val Thr
        130                 135                 140

Gln Ser Gln Pro Leu Gly Ala Val Pro Leu Pro Ala Asp Cys Val
145                 150                 155                 160

Leu Ser Thr Leu Cys Leu Asp Ala Ala Cys Pro Asp Leu Pro Thr Tyr
                165                 170                 175

Cys Arg Ala Leu Arg Asn Leu Gly Ser Leu Leu Lys Pro Gly Gly Phe
                180                 185                 190

Leu Val Ile Met Asp Ala Leu Lys Ser Ser Tyr Tyr Met Ile Gly Glu
                195                 200                 205

Gln Lys Phe Ser Ser Leu Pro Leu Gly Arg Glu Ala Val Glu Ala Ala
        210                 215                 220

Val Lys Glu Ala Gly Tyr Thr Ile Glu Trp Phe Glu Val Ile Ser Gln
225                 230                 235                 240

Ser Tyr Ser Ser Thr Met Ala Asn Asn Glu Gly Leu Phe Ser Leu Val
                245                 250                 255

Ala Arg Lys Leu Ser Arg Pro Leu
        260

<210> SEQ ID NO 2
<211> LENGTH: 1579
<212> TYPE: DNA
<213> ORGANISM: Homo Sapiens

<400> SEQUENCE: 2
gaggaggtgc ttgccagaca ctgggtcatg gcagtggtcg gtgaagctgc agttgcctag     60
ggcagggatg gagagagagt ctgggcatga ggagagggtc tcgggatgtt tggctggact    120
agattttaca gaaagcctta tccaggcttt taaaattact cttccagac ttcatctgag     180 actccttctt cagccaacat tccttagccc tgaatacatt tcctatcctc atctttccct    240
tctttttttt cctttctttt acatgtttaa atttaaacca ttcttcgtga cccctttttct   300 tgggagattc atggcaagaa cgagaagaat gatggtgctt gttaggggat gtcctgtctc    360
tctgaacttt ggggtcctat gcattaaata attttcctga cgagctcaag tgctccctct    420
ggtctacaat ccctggcggc tggccttcat cccttgggca agcattgcat acagctcatg    480
gccctccctc taccataccc tccaccccg ttcgcctaag ctcccttctc cgggaatttc     540
atcatttcct agaacagcca gaacatttgt ggtctatttc tctgttagtg tttaaccaac    600
catctgttct aaaagaaggg ctgaactgat ggaaggaatg ctgttagcct gagactcagg    660
aagacaactt ctgcagggtc actccctggc ttctggagga aagagaagga gggcagtgct    720
ccagtggtac agaagtgaga cataatggaa tcaggcttca cctccaagga cacctatcta    780
agccatttta accctcggga ttacctagaa aaatattaca agtttggttc taggcactct    840
gcagaaagcc agattcttaa gcaccttctg aaaaatcttt tcaagatatt ctgcctagac    900
ggtgtgaagg gagacctgct gattgacatc ggctctggcc ccactatcta tcagctcctc    960
tctgcttgtg aatcctttaa ggagatcgtc gtcactgact actcagacca gaacctgcag   1020
gagctggaga gtggctgaa gaaagagcca gaggcctttg actggtcccc agtggtgacc    1080
tatgtgtgtg atcttgaagg gaacagagtc aagggtccag agaaggagga gaagttgaga   1140
caggcggtca agcaggtgct gaagtgtgat gtgactcaga gccagccact gggggccgtc   1200
```

```
cccttacccc cggctgactg cgtgctcagc acactgtgtc tggatgccgc ctgcccagac    1260
ctccccacct actgcagggc gctcaggaac ctcggcagcc tactgaagcc aggggcttc    1320 ctggtgatca tggatgcgct caagagcagc tactacatga ttggtgagca gaagttctcc    1380
agcctccccc tgggccggga ggcagtagag gctgctgtga aagaggctgg ctacacaatc    1440
gaatggtttg aggtgatctc gcaaagttat tcttccacca tggccaacaa cgaaggactt    1500
ttctccctgg tggcgaggaa gctgagcaga ccctgtgat gcctgtgacc tcaattaaag    1560
caattccttt gacctgtca                                                 1579
```